United States Patent [19]

Yamato et al.

[11] Patent Number: 5,217,961

[45] Date of Patent: Jun. 8, 1993

[54] CONDENSED QUINOLINE SYSTEM N-GLYCOSIDES

[75] Inventors: Masatoshi Yamato; Kuniko Hashigaki, both of Okayama, Japan

[73] Assignee: Mect Corporation, Tokyo, Japan

[21] Appl. No.: 759,615

[22] Filed: Sep. 16, 1991

Related U.S. Application Data

[63] Continuation of Ser. No. 451,363, Dec. 15, 1989, abandoned.

[30] Foreign Application Priority Data

Dec. 27, 1988 [JP]  Japan .................................. 63-330674
Oct. 30, 1989 [JP]  Japan .................................... 1-282208

[51] Int. Cl.$^5$ ..................... A61K 31/47; A61K 31/70; C07H 15/24
[52] U.S. Cl. ...................................... 514/43; 514/42; 536/18.7; 536/29.2; 546/70
[58] Field of Search .................. 514/285, 284, 42–43; 546/70; 536/18.7, 22

[56] References Cited

U.S. PATENT DOCUMENTS

4,826,850  5/1989  Yamato ............................... 514/284

FOREIGN PATENT DOCUMENTS

0095355  11/1983  European Pat. Off. .
238079  10/1988  Japan .................................... 546/62

OTHER PUBLICATIONS

Journal of Medicinal Chemistry, vol. 30, 1987 pp. 1576–1581, G. W. Rewcastle, et al.

Primary Examiner—Johnnie R. Brown
Assistant Examiner—Gary L. Kunz
Attorney, Agent, or Firm—Oblon, Spivak, McClelland, Maier & Neustadt

[57] ABSTRACT

The present invention provides condensed quinoline compounds represented by the following general formula (I):

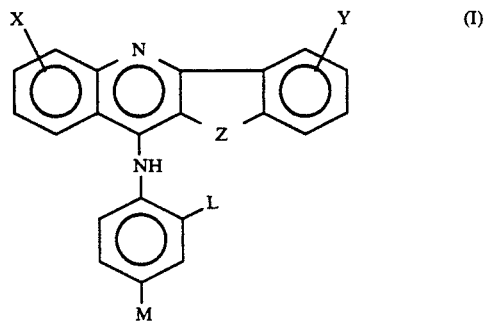

in which Z is NH, X is hydrogen, L is lower alkoxy, M is NHQ, Q is $-SO_2CH_3$, Y is $-NHR$, and R is:

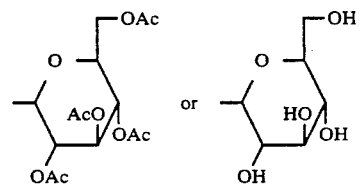

These compounds are effective for inhibiting KB-cell growth and prolongation of the life span of mice implanted with tumor P-388.

4 Claims, No Drawings

CONDENSED QUINOLINE SYSTEM N-GLYCOSIDES

This application is a continuation of application Ser. No. 07/451,363, filed on Dec. 15, 1989, now abandoned.

BACKGROUND OF THE INVENTION

1. Field of the Invention

The present invention relates to novel quinoline system compounds and a process for preparing the same and more particularly, relates to novel indenoquinoline system compounds (Z=CH$_2$), indoloquinoline system compounds (Z=NH), benzothienoquinoline system compounds (Z=S) and benzofuranoquinoline system compounds (Z=O), and a process for preparation thereof.

2. Description of the Related Art

In 1972, B. F. Cain, G. J. Atwell and R. N. Sealye synthesized acridine derivatives each having an alkylamino group at position 9 of acridine, and found that some of them had antileukemia activities. (See J. Med. Chem. vol.15, 611 (1972))

B. F. Cain, G. J. Atwell and R. N. Sealye replaced the alkylamino group at the 9-position of acridine with another molecule or group, and found that N-[4-(9-acridylamino)-3-methoxyphenyl)methanesulfonamide (Amsacrine) has the highest carcinostatic function. (Refer to J. Med. Chem. vol.17, 922 (1974))

G. W. Rewcastle, B. C. Baguley, G. J. Atwell and W. A. Denny modified Amsacrine molecule to synthesize derivatives each having acridine ring introduced with methyl group or N-methylcarbamoyl group, and found that the derivatives have strong carcinostatic activities. (See J. Med. Chem. vol. 30, 1576 (1987))

We previously synthesized indenoquinoline system compounds having high carcinostatic activities, and filed a patent application relating thereto (Japanese Patent disclosure No. 63-101369).

Further, we synthesized benzofuranoquinoline and benzothieoquinoline system compounds having similar high carcinostatic activities, and filed another patent application relating thereto (Japanese Patent disclosure No. 63-238079).

We also filed a patent application directing to indoloquinoline and benzoacridine system compounds, a process for preparation thereof and use of the same as anticancer agents (Japanese Patent disclosure No. 63-56883).

SUMMARY OF THE INVENTION

An object of the present invention is to provide novel quinoline system compounds with strong carcinostatic activities.

The present invention is based on our further investigations on various condensed quinoline system compounds, and we found novel condensed quinoline system compounds and a process for preparing thereof.

According to this invention, there is provided a condensed quinoline system compound represented by the following formula [I]:

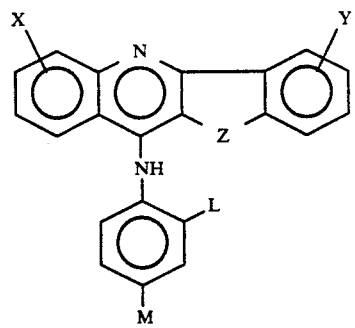

In the formula, L represents a lower alkoxyl group or a dimethylamino group, M represents a hydroxyl group, a methoxycarbonyl group or —NHQ (in this formula, Q represents hydrogen, —SO$_2$CH$_3$, —COOCH$_3$, —COCH$_3$, —CH$_2$SO$_2$Na or —CH$_2$COOH), X represents hydrogen or a lower alkyl group, Y represents hydrogen, a lower alkyl group, halogen, —NO$_2$ or —NHR (in this formula, R represents hydrogen, —COCH$_3$, —SO$_2$CH$_3$,

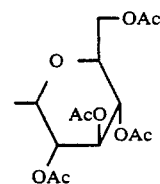

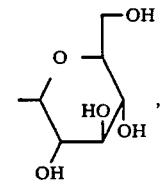

The present invention will now be described in detail.

In the formula [I], the lower alkoxyl group means an alkoxyl group having 1 to 6 carbon atoms. Examples of the alkoxyl group include methoxy, ethoxy, propoxy, butoxy and pentoxy. The lower alkyl means an alkyl group having 1 to 6 carbon atoms. Examples of the alkyl group include methyl, ethyl, n-propyl, iso-propyl, n-butyl, tert-butyl, n-pentyl, n-hexyl. Examples of halogen include fluorine, chlorine, bromine and iodine.

The present invention includes salts, in particular pharmaceuticaly acceptable salts of the compound represented by formula [I]. Examples of the salts include salts of inorganic acids such as hydrochloric acid, phosphoric acid, bromic acid and sulfuric acid, and salts of organic acids such as benzoic acid, citric acid, succinic acid, acetic acid, tartaric acid and maleic acid.

In the case of indenoquinoline system compounds represented by formula [I] wherein Z is CH$_2$, preferably, L is a lower alkoxyl group or a dimethylamino group, M is —NHQ (in this formula, Q represents hydrogen, SO$_2$CH$_3$, —COOCH$_3$, —CH$_2$SO$_2$Na or —CH$_2$COOH), X is hydrogen or a lower alkyl group, Y is hydrogen or a lower alkyl group. The position of X (7- to 10-position) and that of Y (1- to 4-position) are not limited, but it is preferred that X is located at 10-position and Y is located at 1-, 2- and 3-position.

In the case of indoloquinoline system compounds represented by formula [I] wherein Z is NH, preferably, L is a lower alkoxyl group, M is a hydroxyl group, a methoxycarbonyl group or —NHQ ( in this formula, Q represents —SO$_2$CH$_3$, —COOCH$_3$, —COCH$_3$), X is hydrogen or a lower alkyl group, Y is hydrogen, a lower alkyl group, halogen, —NO$_2$ or —NHR (in this formula, R represents —COCH$_3$, —SO$_2$CH$_3$,

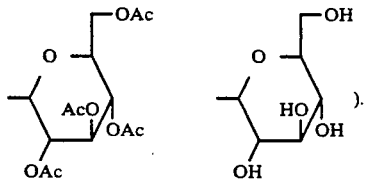
).

The position of X (7- to 10-position) and that of Y (1- to 4-position) are not limited, but it is preferred that X is located at 10-position and Y is located at 1-, 2- and 3-position.

In the case of benzothienoquinoline system compounds represented by formula [I] wherein Z is sulfur, preferably, L is a lower alkoxyl group, M is —NHQ (in this formula, Q represents —SO$_2$CH$_3$), X is hydrogen or a lower alkyl group, Y is hydrogen or a lower alkyl group. The position of X (7- to 10-position) and that of Y (1- to 4-position) are not limited, but it is preferred that X is located at 10-position and Y is located at 1-, 2- and 3-position.

In the case of benzofuranoquinoline system compounds represented by formula [I] wherein Z is oxygen, preferably, L is a lower alkoxyl group, M is —NHQ (in this formula, Q represents —SO$_2$CH$_3$), X is hydrogen or a lower alkyl group, Y is hydrogen or a lower alkyl group. The position of X (7- to 10-position) and that of Y (1- to 4-position) are not limited, but it is preferred that X is located at 10-position and Y is located at 1-, 2- and 3-position.

A process for preparation of the compounds of this invention will be explained in view of schemes 1 to 4 below:

Scheme 1

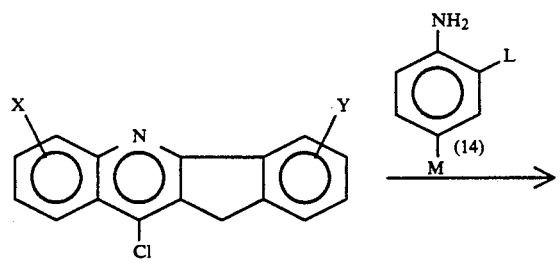

-continued
Scheme 1

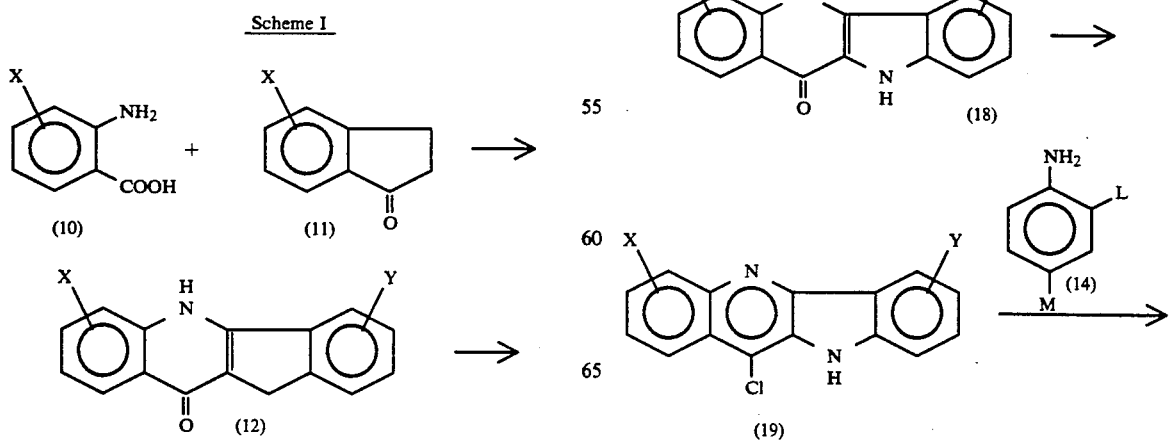

Scheme 2

5,217,961
5
-continued
Scheme 2
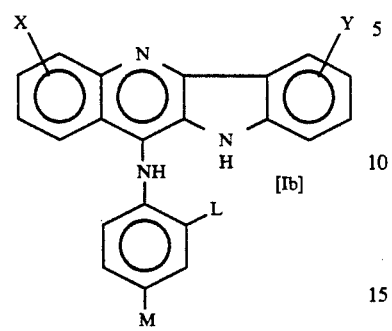
[Ib]
6
-continued
Scheme 3
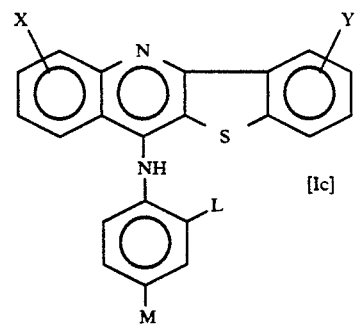
[Ic]
Scheme 3
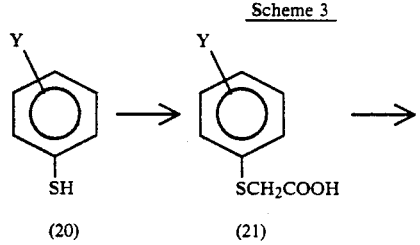
(20)    (21)
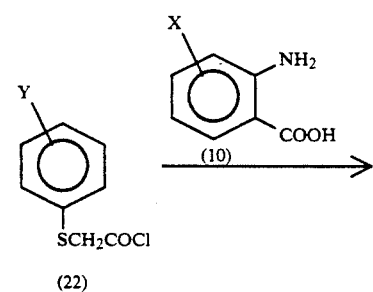
(22)    (10)
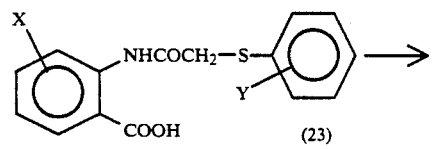
(23)
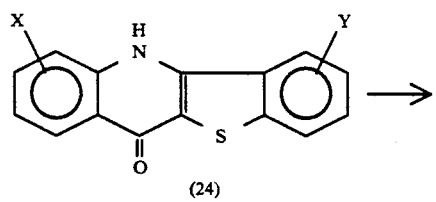
(24)
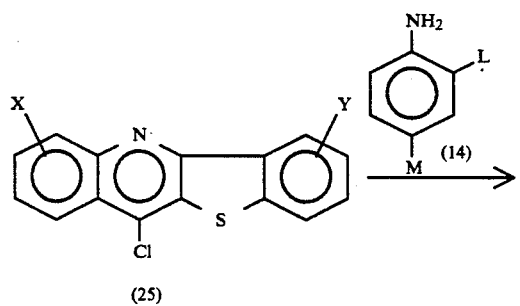
(25)    (14)
Scheme 4
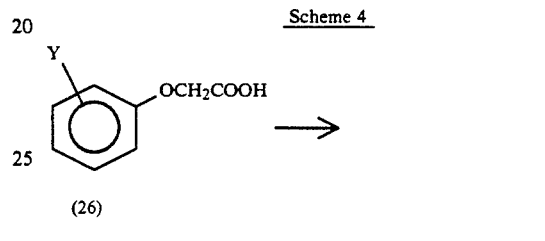
(26)
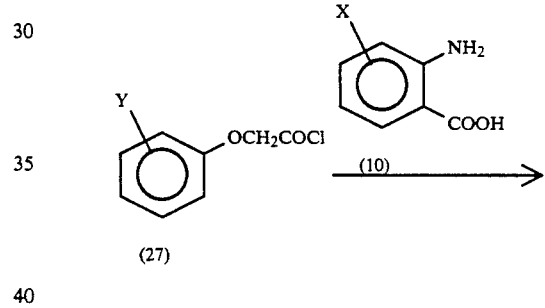
(27)    (10)
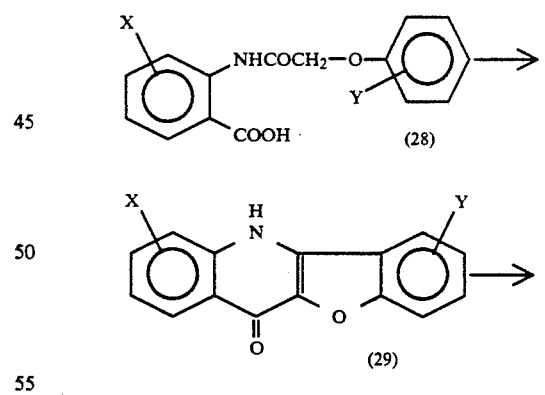
(28)
(29)
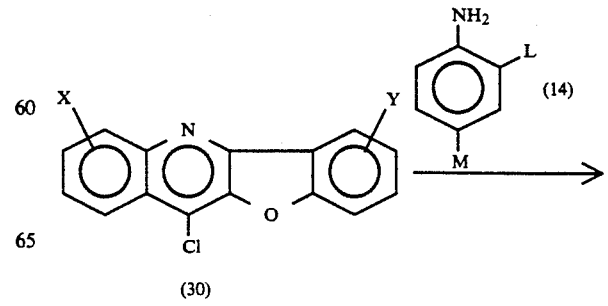
(30)    (14)

-continued
Scheme 4

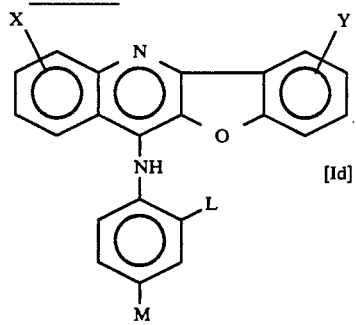

Scheme 1: Indenoquinoline Compound (Z=CH$_2$)

Indenoquinoline compounds represented by formula [Ia] can be synthesized by the method shown in Scheme 1.

Anthranilic acid shown by formula (10) is reacted with indanone shown by formula (11) to obtain indeno[3,2-b]-6, 11-dihydroquinoline-6-one shown by formula (12). The reaction condition should be changed in accordance with kinds of substituents X and Y, and this reaction can be conducted, for example, in the absence or presence of solvent such as para-cymene and at a temperature of from 100° to 200° C.

Compound (12) is then reacted with phosphorus oxychloride to obtain indeno[3,2-b]quinoline shown by formula (13). This reaction is suitably carried out at a reflux temperature.

Thus obtained compound (13) is reacted with an aniline derivative shown by formula (14) to obtain an indenoquinoline compound represented by formula [Ia]. This reaction can be conducted by heating under reflux in the presence of solvent such as dimethylformamide (DMF), pyridine, ethoxyethanol or dioxane, in an atmosphere of inert gas. The reaction product is optionally purified by a conventional method such as recrystallization.

Salts of indenoquinoline compound represented by formula [Ia] can be obtained by addition of an acid such as hydrochloric acid to the reaction solution before, during or after the reaction with the aniline derivative.

Scheme 2: Indoloquinoline Compound (Z=NH)

Indenoquinoline compounds represented by formula [Ib] can be synthesized by the method shown in Scheme 2.

Anthranilic acid shown by formula (10) is reacted with chloroacetyl chloride to obtain N(chloroacetyl)anthranilic acid shown by formula (15). This reaction is suitably carried out by heating under reflux in a solvent such as benzene.

Thus obtained compound (15) is reacted with an aniline derivative shown by formula (16) to obtain an anthranilic acid shown by formula (17). This reaction is suitalby conducted by heating at a temperature from about 50° to 100° C. in a solvent such as dimethylformamide.

Compound (17) is reacted with polyphosphoric acid to obtain an indoloquinoline derivative shown by formula (18). This reaction is suitalby conducted by heating at a temperature from about 100° to 150° C. in the presence of excess amount of polyphosphoric acid.

Compound (18) is reacted with phosphorus oxychloride in the presence of phosphorus pentachloride to obtain a chloride of indoloquinoline derivative shown by formula (19). This reaction is suitably carried out by heating preferably at a reflux temperature.

Thus obtained compound (19) is reacted with an aniline derivative shown by formula (14) to obtain an indoloquinoline compound represented by formula [Ib]. This reaction can be conducted by heating, preferably at a reflux temperature, in the presence of solvent such as dimethylformamide (DMF), pyridine, ethoxyethanol or dioxane, in an atmosphere of inert gas. The reaction product is optionally purified by a conventional method such as recrystallization. Salts of indoloquinoline compound represented by formula [Ib] can be obtained by addition of an acid such as hydrochloric acid to the reaction solution before, during or after the reaction with the aniline derivative.

Scheme 3: Benzothienoquinoline Compound (Z=S)

Benzothienoquinoline compounds represented by formula [Ic] can be synthesized by the method shown in Scheme 3.

A thiol derivative shown by formula (20) is reacted with butyl bromoacetate by a conventional method and then hydrolyzed to obtain α-phenythioacetic acid shown by formula (21). Compound (21) is reacted with thionyl chloride by a conventional method to obtain an acetyl chloride shown by formula (22).

Compound (22) is reacted with anthranilic acid shown by formula (10) to obtain an anthranilic acid derivative shown by formula (23). This reaction can be carried out by dissolving anthranilic acid (10) in an aqueous solution of an alkali hydroxide such as sodium hydroxide, droping compound (22) into this solution and stirring the resulting solution. The droping and stirring are preferably conducted under cooling, for example in an ice bath.

The resultant anthranilic acid derivative (23) is reacted with polyphosphoric acid to obtain an benzothienoquinoline derivative shown by formula (24). This reaction is suitalby conducted by heating at a temperature from about 100° to 150° C. in the presence of excess amount of polyphosphoric acid.

Compound (24) is reacted with phosphorus oxychloride to obtain a chloride of benzothienoquinoline derivative shown by formula (25). This reaction is suitably carried out by heating under reflux in the presence of excess amount of phosphorus oxychloride.

Thus obtained compound (25) is reacted with an aniline derivative shown by formula (14) to obtain a benzothienoquinoline compound represented by formula [Ic]. This reaction can be conducted by heating, for exampl at a reflux temperature, in the presence of solvent such as dimethylformamide (DMF), pyridine, ethoxyethanol or dioxane, in an atmosphere of inert gas. The reaction product is optionally purified by a conventional method such as recrystallization.

Salts of benzothienoquinoline compound represented by formula [Ic] can be obtained by addition of an acid such as hydrochloric acid to the reaction solution before, during or after the reaction with the aniline derivative.

Scheme 4: Benzofuranoquinoline Compound (Z=O)

Benzofuranoquinoline compounds represented by formula [Id] can be synthesized by the method shown in Scheme 4.

Phenoxyacetic acid shown by formula (26) is reacted with thionyl chloride by a conventional method to obtain phenoxyacetyl chloride shown by formula (27).

Phenoxyacetyl chloride (27) is reacted with anthranilic acid shown by formula (10) to obtain an anthranilic acid derivative shown by formula (28). This reaction can be carried out by dissolving anthranilic acid (10) in an aqueous solution of an alkali hydroxide such as sodium hydroxide, droping chloride (28) into this aqueous solution and stirring the resulting solution.

The resultant anthranilic acid derivative (28) is reacted with polyphosphoric acid to obtain an benzofuranoquinoline derivative shown by formula (29). This reaction can be conducted by heating at a temperature of from about 100° to 150° C. in the presence of excess amount of polyphosphoric acid.

Compound (29) is reacted with phosphorus oxychloride to obtain a chloride of benzofuranoquinoline derivative shown by formula (30). This reaction can be carried out by heating in the presence of excess amount of phosphorus oxychloride at a reflux temperature.

Thus obtained compound (30) is reacted with an aniline derivative shown by formula (14) to obtain a benzofuranoquinoline compound represented by formula [Id]. This reaction can be conducted by heating, for exampl at a reflux temperature, in the presence of solvent such as dimethylformamide (DMF), pyridine, ethoxyethanol or dioxane, in an atmosphere of inert gas. The reaction product is optionally purified by a conventional method such as recrystallization.

Salts of benzofuranoquinoline compound represented by formula [Id] can be obtained by addition of an acid such as hydrochloric acid to the reaction solution before, during or after the reaction with the aniline derivative.

Starting materials used in the above-mentioned method are known compounds or compounds easily obtainable by known methods.

The novel condensed quinoline system compounds of this invention suppress proliferation of cancer cells and exhibit effects in prolonging the life of animals with cancer and therefore, are expected to be utilized as unticancer agents.

The present invention will now be described more in detail with reference to Examples.

EXAMPLE 1

Synthesis of hydrochloride of 6-4-(methanesulfonamide-2-methoxyanilino)-1,10-dimethylindeno[3,2-b]quinoline:

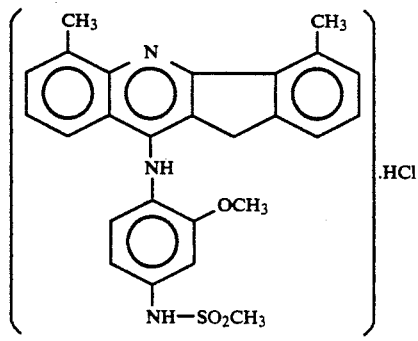

7-Methyl-1-indanone 5 g (34.0 mmol) and 3-methylanthranilic acid 11.0 g (85.0 mmol) were dissolved in 20 ml of paracymene and heated under reflux at 200° to 220° C. for 4 hours. After reflux, paracymene was distilled under the reduced pressure and the resulting residue was recrystallized from toluene to obtain 1,10-dimethylindeno[3,2-b]-6,11-dihydroquinoline-6-one 890 mg (yield: 12%). 7-Methyl-1-indanone was synthesized by the method reported by B. R. Holt and J. London [Zh. Obshch. Khim., 20, 1245(1950)].

The resultant compound 890 mg (3.41 mmol) was refluxed with phosphorus oxychloride 10 ml for 2 hours and unreacted phosphorus oxychloride was distilled off. The residue was poured into ice water and neutralized with KOH. Then the neutralized solution was subjected to extraction with chloroform, and the resulting chloroform solution was washed with an aqueous solution saturated with NaCl and dried with anhydrous MgSO₄. The solvent in the dried solution was then distilled off. The residue was recrystallized from dichloromethane/hexane to obtain 6-chloro-1,10-dimethylindenone 780 mg (yield: 82%) (melting point: 161° to 162° C.).

Then the resulting compound 750 mg and 4-amino-3-methoxyanilinemethanesulfonaminde 610 mg were dissolved in 10 ml of ethoxyethanol under heating. One drop of conc. hydrochloric acid was added to the solution and heated with agitation for 2 hours. Deposited precipitate was collected by filtration and recrystallized from dimethylformamide/methanol to obtain the above captioned compound (hydrochloride) 680 mg (yield : 51%).

Melting point: 232° to 233° C.

I R $\nu_{max}^{Nujol}$ cm$^{-1}$: 3520, 3330, 1320, 1150

$^1$H-NMR(CF$_3$COOD) δ:
2.92,3.11(6 H, each s, CH$_3$×2)
3.33(3 H, s, SO$_2$CH$_3$)
3.52(2 H, s, CH$_2$)
3.93(2 H, s, OCH$_3$)
7.01-7.40(5 H, m, aromatic H, NH)
7.48-7.95(7 H, m, aromatic H )

EXAMPLE 2

Synthesis of hydrochloride of 6-4-(methanesulfonamide-2-methoxyanilio)-10-methylindeno[3,2-b]quinoline:

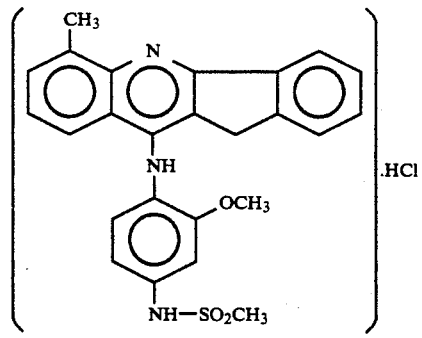

1-Indanone 1 g (7.6 mmol) and 3-methylanthranilic acid 1.1 g (7.3 mmol) were dissolved in 20 ml of paracymene and refluxed at 200° C. for 30 minutes. After reflux, the reaction solution was cooled and deposited crystals were colloected by filtration and washed with pyridine and ether to obtain 10-methylindeno[3,2-b]-6,11-dihydroquinoline-6-one (melting point: 300° C. or more) 960 mg (yield: 53%).

The resultant compound 950 mg (3.85 mmol) was refluxed with phosphorus oxychloride 10 ml for 2 hours and unreacted phosphorus oxychloride was distilled off. The residue was poured into ice water and neutralized with 10% KOH. Then the neutralized solution was subjected to extraction with chloroform, and the resulting chloroform solution was washed with water and dried with anhydrous MgSO4. The solvent in the dried solution was then distilled off to obtain 6-chloro-10-methylindenone 800 mg (yield: 82%) (melting point: 131° to 133° C.). Then the resulting compound 700 mg and 4-amino-3-methoxyanilinemethanesulfonaminde 700 mg (3.30 mmol) were dissolved in 8 ml of ethoxyethanol under heating. Two drops of conc. hydrochloric acid were added to the solution and heated for 4 hours. Deposited precipitate was filtered and recrystallized from methanol to obtain the above captioned compound (hydrochloride) 320 mg (yield: 26.4%).

Melting point: 251° to 253° C.
I R $\nu_{max}^{Nujol}$ cm$^{-1}$: 3340, 1320, 1150
$^1$H-NMR(CF3COOD) δ:
2.92(3 H, s, CH3)
3.33(3 H, s, SO2CH3)
3.52(2 H, s, CH2)
3.93(3 H, s, OCH3)
7.01–7.40(5 H, m, aromatic H, NH)
7.48–7.95(7 H, m, aromatic H )
8.10–8.40(2 H, m, aromatic H )

EXAMPLE 3

Synthesis of hydrochloride of 6-(4-methoxycarbamoyl-2-methoxyanilino)-indeno[3,2-b]quinoline:

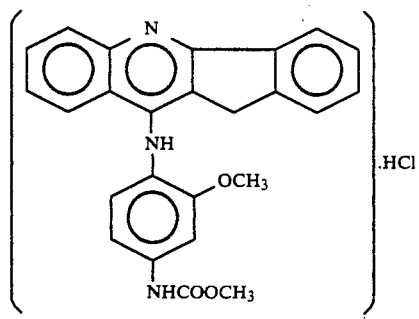

6-Chloroindeno[3,2-b]quinoline (synthesized by a method described in Japanese Patent Disclosure No.63-101369) 700 mg (2.8 mmol) and 4-methoxycarbamoyl-2-methoxyaniline 650 mg were added to 5 ml of ethoxyethanol. Two drops of conc. hydrochloric acid were added to this solution and reated under reflux for 3 hours. After the reaction, deposited precipitate was filtered and washed with ether to obtain the above captioned hydrochloride 610 mg (yield: 49%).

4-Methoxycarbamoyl-2-methoxyaniline was synthesized by the method of G. W. Rew castle (J. Med. Chem., 30, 1576 (1987)).

Melting point: 244° to 246° C.
I R $\nu_{max}^{Nujol}$ cm$^{-1}$:3450, 1730
$^1$H-NMR(DMSO-d6) δ:
3.40(2 H, s, CH2)
3.82(6 H, s, OCH3, COOCH3)
7.11–7.30(2 H, m, aromatic H)
7.38–7.80(6 H, m, aromatic H)
7.96–8.65(4 H, m, aromatic H, NH)
9.72–9.85(1 H, br, NH)

EXAMPLE 4

Synthesis of hydrochloride of 6-(4-amino-2-methoxyanilino)-indeno[3,2-b]quinoline:

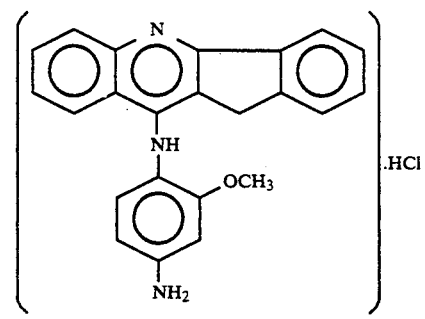

6-(4-Methoxycarbamoyl-2-methoxyanilino)-indeno3,2-b]quinoline (415 mg, 1 mmol) synthesized in Example 3 was dissolved in 4 ml of CH3SO3H. Then, 0.37 ml (5 mmol) of (CH3)2S was added to the resulting solution and stirred at 35° C. for 1.5 hours. The reaction solution was neutralized with KHCO3 and the product was extracted with ethyl acetate. The obtained extract solution was dried with MgSO4 and the solvent was distilled off to obtain the objective product quantitatively.

Melting Point: 246° to 251° C. (decomp,)
I R $\nu_{max}^{Nujol}$ cm$^{-1}$: 3470(NH2), 3440, 3290(NH)
NMR(CDCl3+DMSO−d6) δ:
3.20–3.43(2 H, m, CH2)
3.72(3 H, s, OCH3)
6.14–7.56(11 H, m, aromatic H, NH, NH2)
7.90–8.33(3 H, m, aromatic H )

EXAMPLE 5

Synthesis of hydrochloride of 6-(4-methanesulfonamide-anilino)-indeno[3,2-b]quinoline:

In accordance with the procedures of Example 2 excepting that anthranilic acid was used in place of 3-methylanthranilic acid, hydrchlorate of 6-(4-methanesulfonamide-anilino)-indeno[3,2-b]quinoline was obtained.

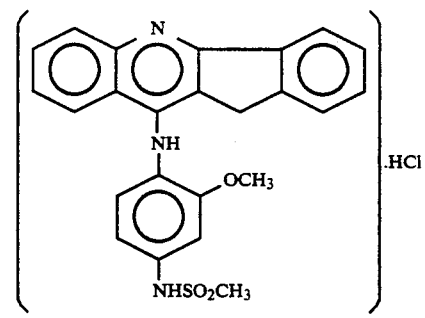

Melting Point: 185° to 188° C.
I R $\nu_{max}^{Nujol}$ cm$^{-1}$:3560, 1335, 1145
NMR(DMSO−d6) δ:
3.08(3 H, s),
3.70(2 H, s),
7.00–7.31(4 H, m),
7.31–7.80(5 H, m),
8.15–8.50(3 H, m)

EXAMPLE 6

Synthesis of hydrochloride of 6-(4-methanesulfonamide-2-dimethylaminoanilino)-indeno[3,2-b]quinoline:

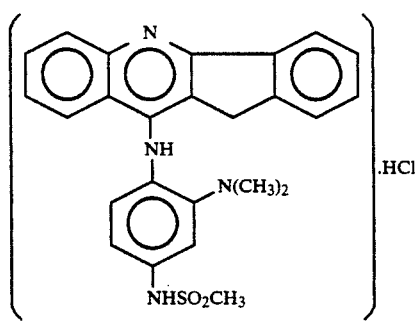

6-Chloroindeno[3,2-b]quinoline (592 mg, 2 mmol) synthesized in Example 3 and hydrochlorate of 4-amino-3-dimethylaminoanilinemethanesulfonamide 519 mg (2 mmol) were added to 10 ml of ethoxyethanol and three drops of conc. hydrochloric acid were added to this solution. Thus obtained solution was heated under reflux for 11 hours. After reflux, deposited crystals were collected and washed with ether to obtain the objective product 520 mg (yield: 59%).

Melting point: 262° to 265° C.
I R $\nu_{max}^{Nujol}$ cm$^{-1}$:3340, 1330, 1148
NMR(DMSO—d$_6$) δ:
2.69(6 H, s, NMe$_2$)
3.15(3 H, s, SO$_2$Me)
3.20–3.38(2 H, m, CH$_2$)
6.80–7.83(8 H, m, aromatic H)
8.11–8.98(3 H, m, aromatic H)
9.89–10.03(1 H, br, NH)
10.34–10.51(1 H, br, NHSO$_2$—)

EXAMPLE 7

Synthesis of hydrochloride of 6-(4-sodium sulfonmethylamino-2-methoxyanilino)-indeno[3,2-b]quinoline:

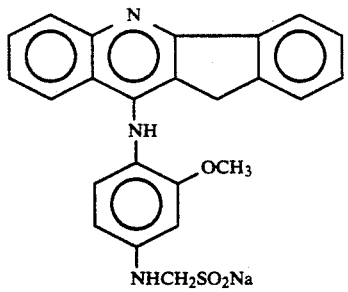

6-(4-Amino-2-methoxyanilino)-indeno[3,2-b]quinoline (353 mg, 1 mmol) synthesized in Example 4 was dissolved in 60 ml of ethanol. 30 ml of ethanol solution (ethanol: water=8:2) of HOCH$_2$SO$_2$Na (150 mg, 1.1 mmol) was added to this solution. The resulting reaction mixture was heated at 60° to 70° C. for 10 minutes. After heating, deposited crystals were collected by filtration and washed with ethanol and ether to obtain the objective product 339 mg (Yield: 75%).

The product was identified by confirming generation of SO$_2$ when the product was heated in 10% HCl solution at 100° C.

EXAMPLE 8

Synthesis of hydrochloride of 6-(4-carboxymethylamino-2-methoxyanilino)-indeno[3,2-b]quinoline:

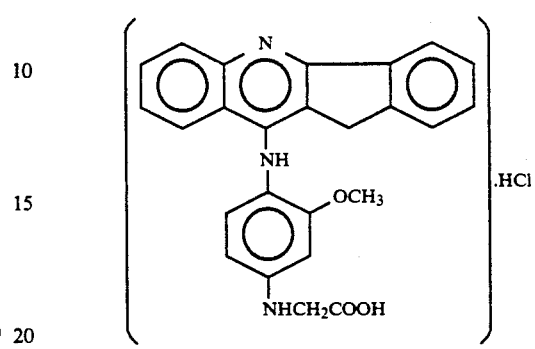

6-(4-Amino-2-methoxyanilino)-indeno[3,2-b]quinoline (500 mg, 1.4 mmol) synthesized in Example 4 was dissloved in 5 ml of dried DMF and 500 mg (3.5 mmol) of K$_2$CO$_3$ was added to this solution. To this mixing solution, BrCH$_2$COOCH$_3$ 0.16 ml (1 5mmol) was added and heated at 50° to 60° C. for 2 hours. After heating, the reaction mixture was poured into ice water and subjected to extraction with ethyl acetate. The extract solution was dried with MgSO$_4$ and the solvent was distilled off to obtain quantitatively 6-(4-methylcarboxymethylamino-2-methoxyanilino)-indeno[3,2-b]quinoline.

426 mg (1 mmol) of this product was dissloved in 20% NaOH-methanol solution 10 ml and agitated for 2 hours at room temperature. After agitation, the reaction mixture was neutralized with 10% HCl solution and then methanol was distilled off. Then 1 ml of 10% HCl solution was added to the residue to acidify and deposited crystals were collected by filtration to obtain the objective product (hydrochloride) 306 mg (yield: 74%).

Physical properties of 6-(4-methylcarboxymethylamino-2-methoxyanilino)-indeno3,2-b]quinoline:

Melting point: 260° to 270° C. (decomp)
I R $\nu_{max}^{Nujol}$ cm$^{-1}$: 1740(C$_2$O), 3400(NH)
$^1$H-NMR(CDCl$_3$) δ:
3.42(2 H, s, CH$_2$)
3.77(6 H, s, OCH$_3$)
3.90(2 H, s, CH$_2$)
6.01–6.42(4 H, m, aromatic H, NH)
7.18–7.70(4 H, m, aromatic H, NH)
7.99–8.32 (3 H, m, aromatic H)

EXAMPLE 9

Synthesis of hydrochloride of 6-(4-methanesulfonamide-2-methoxyanilino)-10-methylindolo[3,2-b]quinoline:

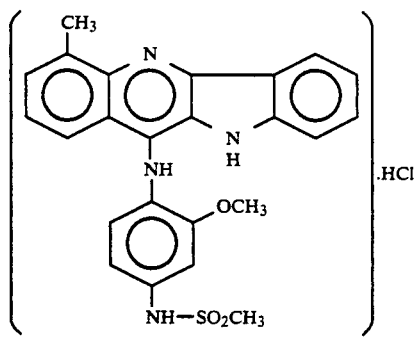

3-Methylanthranilic acid 10 g (0.07 mol) was dissolved in dried benzene 100 ml. To this solution, chloroacetylchloride 5.81 ml (0.07 mol) was added dropwise at room temperature and heated under reflux for two hours. After cooling, deposited crystals were collected by filtration and recrystallized from benzene-toluene to obtain 3-methyl-N(chloroacetyl)anthranilic acid 11.7 g (yield: 79%).

Then, 3 g (0.01 mol) of this compound was dissolved in 5 ml (0.04 ml) of aniline and 5 ml of dimethylformamide and heated at 80° to 90° C. for 4 hours. Cold water was added to the reaction solution, and deposited crystals were collected by filtration, washed with ether and recrystallized from toluene to obtain 3-methyl-N(phenylaminoacetyl)anthranilic acid 2.6 g (yield: 70%).

The resulting compound 2.5 g (7.8 mmol) was mixed with polyphosphoric acid 50 g and heated at 120° C. for 2 hours. After heating, the reaction mixture was poured into cold water. The resulting solution was neutralized with potassium hydrogencarbonate and deposited crystals were collected by filtration to obtain 11-methylindolo3,2-b]-6,11-dihydroquinoline-6-one 1.7 g (yield: 77%).

The resultant compound 1.7 g (6 mmol) was added to phosphorus pentachloride 1.25 g (6 mmol) and phosphorus oxychloride 30 ml, and heated under reflux for 2 hours. Unreacted phosphorus oxychloride was distilled off, and the residue was poured into ice water and neutralized with 10% NaOH solution. Then the neutralized solution was subjected to extraction with chloroform, and the resulting chloroform solution was washed with water, dried with anhydrous MgSO$_4$ and the solvent was distilled off. The residue was recrystallized from dichloromethane/methanol to obtain 6-chloro-10-methylindolo[3,2-b]quinoline (melting point: 228° to 230° C.) 1.2 g (yield: 66%).

Then the resulting compound 800 mg (3.1 mmol) and 4-amino-3-methoxyanilinemethanesulfonaminde 684 mg (3.6 mmol) were dissolved in 10 ml of ethoxyethanol. One drop of conc. hydrochloric acid was added to this solution and heated under reflux for 4 hours. After cooling, precipitate was collected, washed with ether and chloroform and recrystallized from methanol to obtain the objective compound (hydrochloride) 870 mg (yield: 72%).

Melting point: 260° to 263° C.)
I R $\nu_{max}^{Nujol}$ cm$^{-1}$:3120, 1325, 1160
NMR(CDCl$_3$+DMSO—d$_6$) δ:
3.14(3 H, s, CH$_3$)
3.31(3 H, s, SO$_2$CH$_3$)
3.85(3 H, s, OCH$_3$)
7.09-7.45(2 H, m, aromatic H)
7.53-8.18(8 H, m, aromatic H)
8.83-9.04(1 H, m, NH)
9.21-9.46(1 H, m, NH)
10.49-10.60(1 H, br, NH)

EXAMPLE 10

Synthesis of hydrochloride of 6-(4-methanesulfonamide-2-methoxyanilino)-1,10-dimethylindolo[3,2-b]quinoline:

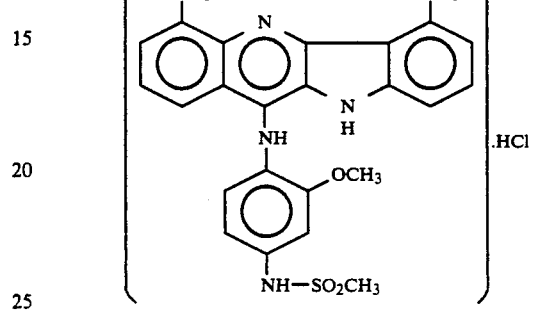

3-Methyl-N(chloroacetyl)anthranilic acid 7.5 g (33 mmol)(synthesized from 3-methylanthranilic acid by the same procedures as those of Example 9) and m-toluidine 11 ml (0.10 mol) were dissolved in 60 ml of dimethylformamide and heated at 90° C. for 4 hours. The reaction solution was poured into ice water and extracted with ether. The resulting ether solution was extracted with 10% sodium hydroxide and the resluting aqueous solution was neutralized with 10% HCl solution. The neutralized solution was extracted with ether, and the ether solution was washed with water and dried. The solvent was distilled off and the residue was recrystallized from benzene-toluene to obtain 3-methyl-N[(3-methylphenyl)acetyl]anthranilic acid 4.8 g (yield: 49%).

The resulting compound 5.1 g (0.02 mmol) was mixed with polyphosphoric acid 200 g and heated at 120° C. for 2 hours. After heating, the reaction mixture was poured into ice water. The resulting solution was neutralized with an aqueous solution saturated with potassium hydrogencarbonate and deposited crystals were collected by filtration to obtain a mixture of 1, 10-dimethyl-6,11-dihydroindolo[3,2-b]-quinoline-6-One and 3, 10-dimethyl-6,11dihydroindolo[3,2-b]-quinoline-6-one (3.9 g (yield: 87.5%)).

The resulting mixture 3.8 g (5 mmol) was added to phosphorus oxychloride 20 ml and heated under reflux for 2 hours. Unreacted phosphorus oxychloride was distilled off under the reduced pressure, and the residue was poured into ice water and neutralized with 10% potassium hydrogencarbonate solution. Then the neutralized solution was subjected to extraction with ethylacetate. The resulting ethylacetate solution was washed with an aqueous solution saturated with NaCl and dried with MgSO$_4$, and the solvent in the dried solution was distilled off. Thus obtained residue was subjected to silica gel column chromatography and separated with hexane (eluent) to obtain 6-chloro-1,10-dimethylindolo[3,2-b]quinoline 620 mg (yield: 15%) and 6-chloro-3,10-dimethylindolo3,2-b]quinoline 560 mg (yield: 14%).

The resulting 6-chloro-1,10-dimethylindolo[3,2-b]quinoline 400 mg (1.43 mmol) and 4-amino-3-methoxyanilinemethanesulfonaminde 340 mg (1.5 mmol) were dissolved in 6 ml of ethoxyethanol. Two drops of conc. hydrochloric acid were added to this solution and heated under reflux for 3 hours. After cooling, precipitate was collected by filtration to obtain the objective compound (hydrochloride) 450 mg (yiled: 63%).

Melting point: 202° to 205° C.
I R $\nu_{max}^{Nujol}$ cm$^{-1}$: 1320, 1150
NMR(CF$_3$COOD) δ:
2.98(3 H, s, CH$_3$)
3.12(3 H, s, CH$_3$)
3.47(3 H, s, SO$_2$CH$_3$)
3.95(3 H, s, OCH$_3$)
7.05–8.03(10 H, m, aromatic H, NH)
8.38–8.55(1 H, m, aromatic H)

EXAMPLE 11

Synthesis of hydrochloride of 6-(4-methanesulfonamide-2-methoxyanilino)-3,10-dimethylindolo[3,2-b]quinoline:

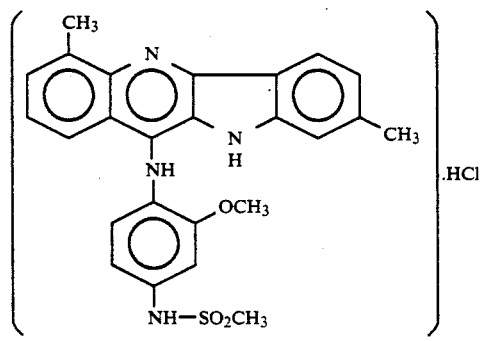

6-Chloro-3,10-dimethylindolo[3,2-b]quinoline 560 mg (1.43 mmol) obtained in Example 10 and 4-amino-3-methoxyanilinemethanesulfonaminde 340 mg (1.5 mmol) were dissolved in 6 ml of ethoxyethanol. Two drops of conc. hydrochloric acid were added to this solution and heated under reflux for 3 hours. After cooling, precipitate was collected by filtration to obtain the objective compound (hydrochloride) 420 mg (yield: 59%).

Melting point: 198° to 200° C.
I R $\nu_{max}^{Nujol}$ cm$^{-1}$:1320, 1150
NMR(CF$_3$COOD) δ:
2.54(3 H, s, CH$_3$)
2.93(3 H, s, CH$_3$)
3.39(3 H, s, SO$_2$CH$_3$)
3.98(3 H, s, OCH$_3$)
7.14–7.96(9 H, m, aromatic H, NH)
8.16–8.47(2 H, m, aromatic H)

EXAMPLE 12

Synthesis of hydrochloride of 2-chloro-6-(4-methanesulfonamide-2-methoxyanilino)indolo[3,2-b]quinoline:

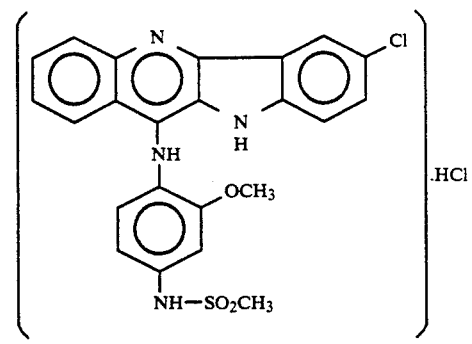

N(chloroacetyl)anthranilic acid 3.2 g (0.02 mol) and p-chloroaniline 3.95 g (0.005 mol) were dissolved in 4 ml of dimethylformamide and heated at 80° to 90° C. for 4 hours. The reaction solution was poured into ice water and deposited crystals were collected by filtration. These crystals were washed with ether and recrystallized from ethanol to obtain N-[(4-chlorophenylamino)acetyl]anthranilic acid 2.2 g (yield: 72.2%).

The resulting compound 2.28 g (7.52 mmol) was mixed with polyphosphoric acid 75 g and heated at 120° C. for 2 hours. After heating, the reaction mixture was poured into ice water and deposited crystals were collected by filtration to obtain 2-chloroindolo[3,2-b]-6,11-dihydroquinoline-6-one 1.6 g (yield: 80%).

The resulting compound 1.34 g (5 mmol) was added to phosphorus oxychloride 10 ml and heated under reflux for 3 hours. An excess amount of phosphorus oxychloride was distilled off, and the residue was poured into ice water and neuralized with potassium hydrogencarbonate. Then the neutralized solution was subjected to extraction with chloroform. The resulting chloroform solution was washed with an aqueous solution saturated with NaCl and dried with anhydrous MgSO$_4$, and the solvent in the dried solution was distilled off. Thus obtained residue was recrystallized from chloroform-methanol to obtain 2,6-dichloroindolo[3,2-b]-quinoline (melting point: 221° to 222° C.) 1.1 g (yield: 74%).

This compound 861 mg (3.01 mmol) and 4-amino-3-methoxyanilinemethanesulfonaminde 680 mg (4.5 mmol) were dissolved in 8 ml of ethoxyethanol. Two drops of conc. hydrochloric acid were added to this solution and heated under reflux for 3 hours. After cooling, deposited crystals were collected by filtration to obtain the objective compound (hydrochloride) 1.01 mg (yiled: 60%).

Melting point: 203.5° to 204° C. (decomp.)
I R $\nu_{max}^{Nujol}$ cm$^{-1}$:3360, 1320, 1150
NMR(DMSO—d$_6$) δ:
3.06(3 H, s, SO$_2$CH$_3$)
3.52(3 H, s, OCH$_3$)
7.01–7.80(7 H, m, aromatic H)
8.11–8.38(2 H, m, aromatic H)
8.61–8.70(1 H, m, NH)
10.04–10.13(1 H, m, NH)
10.51–10.72(1 H, m, NH)

EXAMPLE 13

Synthesis of hydrochloride of 6-(4-methanesulfonamide-2-methoxyanilino)-2-methylindolo[3,2-b]quinoline:

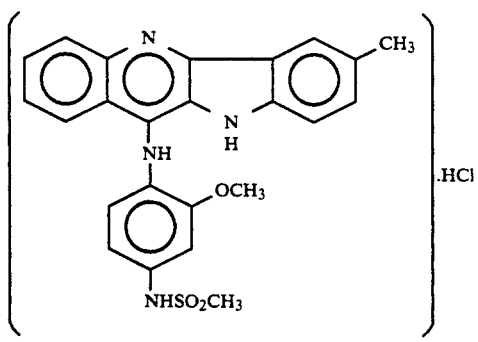

N(chloroacetyl)anthranilic acid 3.2 g (0.02 mol) and p-toluidine 3.4 g (0.005 mol) were dissolved in 4 ml of dimethylformamide and heated at 90° C. for 3 hours. The reaction solution was poured into ice water and deposited crystals were collected by filtration. These crystals were washed with ether and recrystallized from ethanol to obtain N-[(4-methylphenylamino)acetyl]anthranilic acid 2.6 g (yield: 70%).

The resulting compound 2.1 g (7.02 mmol) was mixed with polyphosphoric acid 70 g and heated at 120° C. for 2 hours. After heating, the reaction mixture was poured into ice water and deposited crystals were collected by filtration to obtain 2-methylindolo[3,2-b]-6,11-dihydroquinoline-6-one 1.2 g (yield: 80%).

This compound 1.1 g (4 mmol) was added to phosphorus oxychloride 8 ml and heated under reflux for 3 hours. An excess amount of phosphorus oxychloride was distilled off, and the residue was poured into ice water and neutralized with potassium hydrogencarbonate. Then the neutralized solution was subjected to extraction with chloroform. The resulting chloroform solution was washed with an aqueous solution saturated with NaCl, dried with anhydrous MgSO$_2$ and the solvent in the dried solution was distilled off. Thus obtained residue was recrystallized from chloroformmethanol to obtain 2-mehyl-6-chloroindolo3,2-b1quinoline (melting point: 201° to 203° C.) 1.2 g (yield: 66%).

The resulting compound 660 mg (2.51 mmol) and 4-amino-3-methoxyanilinemethanesulfonaminde 560 mg (2.65 mmol) were dissolved in 8 ml of ethoxyethanol. Two drops of conc. hydrochloric acid were added to this solution and heated under reflux for 2 hours. After cooling, deposited crystals were collected by filtration and recrystallized from methanol to obtain the objective compound (hydrochlorate) 870 mg (yield: 72%).

Melting point: 214° to 217° C.
$^1$H-NMR(DMSO—d$_6$) δ:
2.48(3 H, s, CH$_3$)
3.05(3 H, s, SO$_2$Me)
3.56(3 H, s, OCH$_3$)
6.85-7.50(7 H, m, aromatic H)
8.05-8.46(3 H, m, aromatic H)
9.71-9.82(1 H, m, NH)
10.24-10.30(1 H, m, NH)
10.98-11.10(1 H, br, NH)

EXAMPLE 14

Synthesis of hydrochloride of 6-(4-methoxycarbamoyl-2-methoxyanilino)indolo[3,2-b]quinoline:

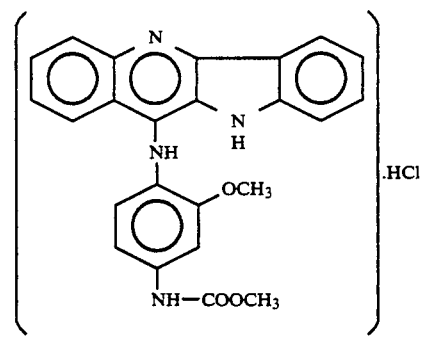

Hydrochlorate of 4-methoxycarbamoyl-2-methoxyaniline 3.3 g [synthesized by the method of Rewcastle et al. (Journal of Medical Chemistry(1987) vol. 30, 1576-1581)] and 6-chloroindolo] 3,2-b]quinoline 3.0 g (12 mmol) were dissolved in 35 ml of ethoxyethanol and heated under reflux for 4 hours. After cooling, deposited crystals were collected by filtration and washed with ether and chloroform. Thus obtained crystals were added to CH$_3$CN—KHCO$_3$ solution and to this solution, a large amount of water was added and deposited crystals were collected by filtration. These crystals were recrystallized from methanol and dichloromethane to obtain the objective compound 3.3 g (yield : 67%).

Melting point: 178° to 181° C.
I R$_{max}^{Nujol}$ cm$^{-1}$: 3390, 1716
NMR(DMSO—d$_6$) δ:
3.71 3.75(6 H, each s, OMe×2)
6.85-7.10(2 H, m, aromatic H)
7.10-8.02(6 H, m, aromatic H)
8.02-8.72(3 H, m, aromatic H)
9.72(1 H, br, NH)
11.03(1 H, br, —NH)

EXAMPLE 15

Synthesis of hydrochloride of 6-(4-acetoamino-2-methoxyanilino)indolo[3,2-b]quinoline:

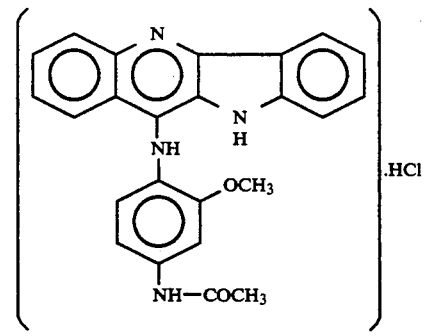

6-(4-Methoxycarbamoyl-2-methoxyanilino)indolo[3,2-b]-quinoline obtained in Example 14 was dissolved in methanesulfonic acid 5 ml in a stream of argon. Then dimethylsulfide 0.37 ml was added dropwise to this solution in an ice bath and stirred at room temperature for one day. After reaction, the solution was neutralized with potassium hydrogencarbonate in a stream of argon and etracted with ethyl acetate. The resulting ethyl acetate solution was washed with water, dried with anhydrous MgSO4 and the solvent was distilled off to obtain 6-(4-amino-2-methoxyanilino)indolo[3,2-b]quinoline. This compound was dissloved in acetic anhydride 0.27 ml/acetic acid 5 ml without purification and reacted by adding gradually with zinc powder 250 mg. After agitation for one hour, the reaction solution was added with water and neutralized with potasisum hydrogencarbonate. Deposited precipitate was collected by filtration and dissloved in methanol. After addition with hydrochloric acid, the resulting methanol solution was concentrated under the reduced pressure to obtain the objective compound (hydrochlorate) 330 mg (yield: 76%).

Melting point: 168° to 173° C.
I $R_{max}^{Nujol}$ cm$^{-1}$: 1650
NMR(CF3COOD+CDCl3) δ:
2.36(3 H, s, —COCH3)
3.87(3 H, s, —OCH3)
6.94–8.44(14 H, m, aromatic H, NH)

EXAMPLE 16

Synthesis of hydrochlorate of 6-(4-methanesulfonamide-2-methoxyanilino)-1-mehtylindolo[3,2-b]quinoline:

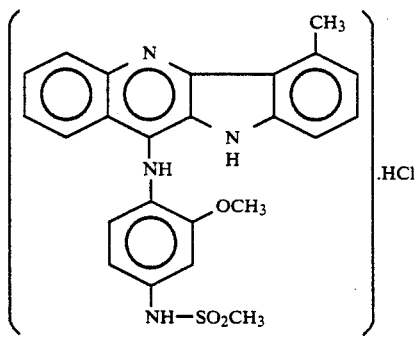

N(chloroacetyl)anthranilic acid 6.4 g (15 mmol) (synthesized from anthranilic acid by the same procedures as those of Example 9) and m-toluidine 9.5 ml (0.09 mol) were dissolved in 60 ml of dimethylformamide and heated at 80° to 90° C. for 4 hours. The reaction mixture was poured into ice water and extracted with ether. The resulting ether solution was extracted with 10% sodium hydroxide and the resulting aqueous solution was neutralized with 10% HCl solution. The neutralized solution was extracted with ether, and the ether solution was washed with water and dried. The solvent of dried solution was distilled off and the residue was recrystallized from benzene-hexane to obtain N[(3-methylphenyl)acetyl]anthranilic acid 4.7 g (yield: 57%).

The resulting compound 5.0 g (0.02 mmol) was mixed with polyphosphoric acid 176 g and heated at 120° C. for 2 hours. After heating, the reaction mixture was poured into ice water. The resulting solution was neutralized with an aqueous solution saturated with potassium hydrogencarbonate and deposited crystals were collected by filtration to obtain a mixture of 1-methyl-6,11-dihydroindolo[3,2-b]-quinoline-6-one and 3-methyl-6,11-dihydroindolo[3,2-b]-quinoline-6-one (4.1 g (yield: 83%)).

The resulting mixture 4.1 g (16 mmol) was added to phosphorus oxychloride 20 ml and heated under reflux for 2 hours. Unreacted phosphorus oxychloride was distilled off under the reduced pressure, and the residue was poured into ice water and neutralized with an aqueous solution saturated with potassium hydrogencarbonate. Then the neutralized solution was subjected to extraction with ethyl acetate. The resulting ethyl acetate solution was washed with an aqueous solution saturated with NaCl, dried with MgSO4 and the solvent in the dried solution was distilled off. Thus obtained residue was subjected to silica gel column chromatography and separated with hexane (eluent) to obtain 6-chloro-1-methylindolo[3,2-b]quinoline (melting point: 170° to 172° C.) 450 mg (yield: 10%) and 6-chloro-3-methylindolo[3,2-b]quinoline (melting point: 193° to 194° C.) 380 mg (yield: 8.4%).

The resulting 6-chloro-1-methylindolo3,2-b]quinoline 400 mg (1.51 mmol) and 4-amino-3-methoxyaniline methanesulfonaminde 360 mg (1.75 mmol) were dissolved in 6 ml of ethoxyethanol. Two drops of conc. hydrochloric acid were added to this solution and heated under reflux for 3 hours. After cooling, precipitate was collected by filtration to obtain the objective compound (hydrochloride) 520 mg (yield: 71%).

Melting point: 214° to 217° C.
NMR(CF3COOD) δ:
3.06(3 H, s, CH3)
3.33(3 H, s, SO2CH3)
3.73(3 H, s, OCH3)
7.08–7.46(7 H, m, aromatic H, NH)
7.60–8.56(6 H, m, aromatic H)

EXAMPLE 17

Synthesis of hydrochloride of 6-(4-methanesulfoneamide-2-methoxyanilino)-3-mehtylindolo[3,2-b]quinoline:

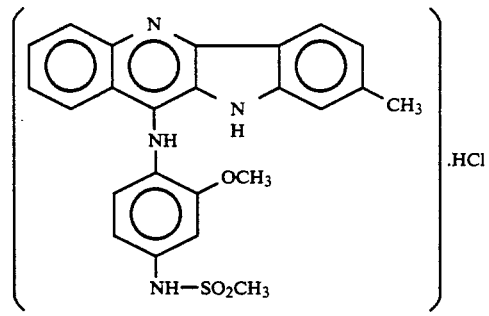

6-Chloro-3-methylindolo[3,2-b)quinoline 350 mg (1.31 mmol) obtained in Example 16 and 4-amino-3-methoxyaniline methanesulfonaminde 310 mg (1.42 mmol) were dissolved in 6 ml of ethoxyethanol. Two drops of conc. hydrochloric acid were added to this solution and heated under reflux for 2 hours. After cooling, precipitate was collected by filtration to obtain the objective compound (hydrochloride) 430 mg (yield: 68%).

Melting point: 215° to 217° C.
NMR(CF3COOD) δ:
2.48(3 H, s, CH3)
3.38(3 H, s, SO2CH3)
3.95(3 H, s, OCH3)
7.07–7.50(6 H, m, aromatic H, NH)
7.60–8.47(7 H, m, aromatic H, NH)

EXAMPLE 18

Synthesis of 6-(4-methanesulfonamide-2-methoxyanilino)-2-nitroindolo[3,2-b]quinoline:

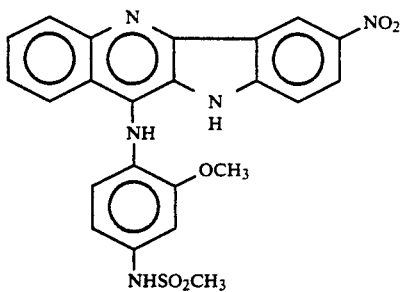

Fuming nitric acid (d=1.42) was added dropwise to 6-chloroindolo[3,2-b]quinoline 2.52 g (0.01 mol) at 0° C. The resulting mixture was left overnight at room temperature and then poured into ice water. Deposited crystals were collected by filteration, washed with an aqueous solution saturated with KHCO₃ and recrystallized from tetrahydrofuran and CH₂Cl₂ to obtain 6-chloro-2nitroindolo[3,2-b]quinoline (melting point: 280° to 290° C. (decomp.)) 2.50 g (yield: 84%).

This compound 5.9 g (0.02 mol) and 4-amino-3-methoxyanilinemethanesulfonaminde hydrochlorate 6 g (0.024 mol) were dissolved in 10 ml of ethoxyethanol and heated under reflux for 6 hours. After cooling, precipitate was collected by filtration and added to chloroform. This chloroform was neutralized with an aqueous solution saturated with KHCO₃ and then chloroform was distilled off. The residue was recrystallized from methanol to obtain the objective compound 6 g (yield : 61%).

Melting point: 300° C. or more
MS m/e: 478 (M⁺)

EXAMPLE 19

Synthesis of hydrochloride of 2-fluoro-6-(4-methanesulfonamide-2-methoxyanilino)indolo[3,2-b]quinoline:

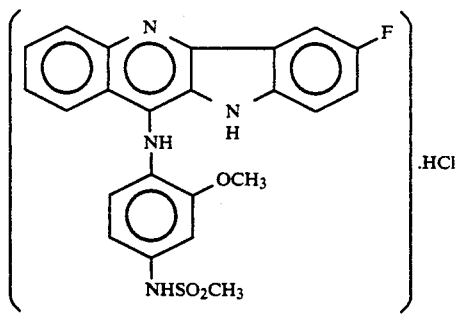

N(chloroacetyl)anthranilic acid 4.0 g (8 mmol) and p-fluoroaniline 5.3 ml (56 mmol) were dissolved in 4 ml of dimethylformamide and heated at 80° to 90° C. for 4 hours. The reaction solution was poured into ice water and deposited crystals were collected by filtration. These crystals were washed with ether and recrystallized from ethanol to obtain N-[(4-fluorophenylamino)acetyl]anthranilic acid (melting point: 217° to 219° C.) 2.4 g (yield: 46%).

The resulting compound 2.26 g (7.5 mmol) was mixed with polyphosphoric acid 75 g and heated at 120° C. for 2 hours. After heating, the reaction mixture was poured into ice water and deposited crystals were collected by filtration to obtain 2-fluoromethylindolo[3,2-b]-6,11-dihydroquinoline-6-one 1.35 g.

The resulting compound 1.0 g was added to phosphorus oxychloride 10 ml and heated under reflux for 3 hours. An excess amount of phosphorus oxychloride was distilled off. The residue was poured into ice water, neutralized with potassium hydrogencarbonate and deposited crystals were collected by filtration. The crystals were subjected silica gel column chromatography to obtain 6-chloro-2-fluoroindolo[3,2-b]quinoline (melting point: 201° to 204° C.) 470 mg (yield: 43%).

This compound 400 mg (3.01 mmol) and 4-amino-3-methoxyanilinemethanesulfonaminde 400 mg (1.6 mmol) were dissolved in 10 ml of ethoxyethanol and heated under reflux for 3 hours. After cooling, deposited crystals were collected by filtration to obtain the objective compound (hydrochloride) 660 mg (yiled: 95%).

Melting point: 260° C. (decomp.)
I R $\nu_{max}^{Nujol}$ cm⁻¹:1150, 1318(SO₂CH₃), 3250(NH₂)
3.12(3 H, s, CH₃)
3.66(3 H, s, CH₃)
6.80-8.02(10 H, m, aromatic H)

EXAMPLE 20

Synthesis of hydrochloride of 6-(4-hydroxy-2-methoxyanilino) indolo[3,2-b]quinoline:

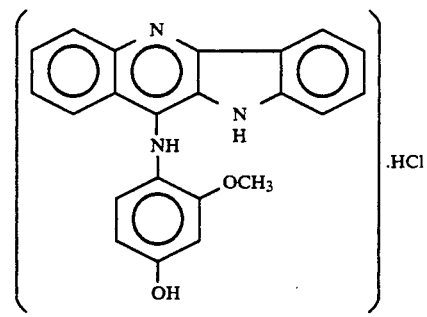

1.4 g (8.3 mmol) of 4-hydroxy-2-methoxyaniline hydrochlorate synthesized by the method of J. L. Jurlina et al. [J. Med. Chem., 1987, Vol. 30, No.3] and 6-chloroindolo[3,2-b]quinoline 1.75 g (6.9 mmol) were dissolved in 10ml of ethoxyethanol and heated under reflux for 4 hours. Deposited crystals were collected by filtration and washed with ether to obtain the objective compound (hydrochloride) 1.8 g (yield: 78%).

Melting point: 259° to 263° C. (decomp.)
¹H-NMR(CF₃COOD) δ:
3.91(3 H, s, OCH₃)
7.10-8.54(14 H, m, aromatic H, NH)

EXAMPLE 21

Synthesis of 6-(4-aceto-2-methoxyanilino)indolo[3,2-quinoline:

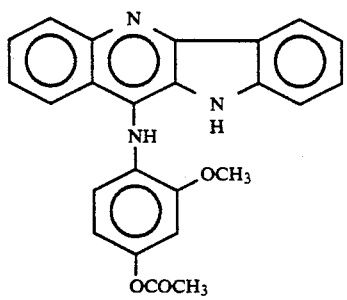

600 mg (1.5 mol) of hydrochloride of 6-(4-hydroxy-2-methoxyanilino)indolo[3,2-b]quinoline obtained in Example 20, anhydrous $K_2CO_3$ 2.1 g and acetic anhydride 0.46 ml were dissolved in 90 ml of dimethylformamide and agitated at room temperature for 1.5 hours. The reaction solution was poured into ice water, and deposited crystals were collected by filtration and recrystallized from tetrahydrofuran and $CH_2Cl_2$ to obtain the objective compound 510 mg (yield: 77%).

Melting point: 224° to 230° C. (decomp.)
2.56(3 H, s, $COCH_3$)
3.95(3 H, s, $OCH_3$)
6.90–8.61(13 H, m, aromatic H, NH)

EXAMPLE 22

Synthesis of 2-amino-6-(4-methanesulfonamide-2-methoxyanilino)indolo[3,2-b]quinoline

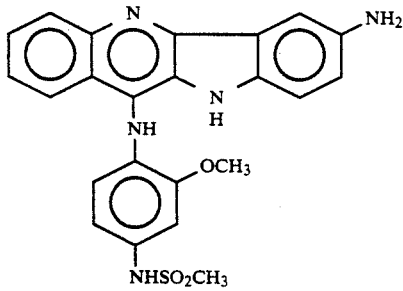

6-(4-Methanesulfonamide-2-methoxyanilino)-2-nitroindolo[3,2-b]quinoline 2 g (3.6 mmol) obtained in Example 18 was dissolved in 150 ml of acetic acid. 10% Pd-C 50 mg was added to this solution and the above compound was reduced by hydrogen for 5 hours. After removal of Pd-C, acetic acid was distilled off, and the residue was neutralized with an aqueous solution saturated with $KHCO_3$ and extracted with chloroform. The resulting chloroform solution was washed with an aqueous solution saturated with NaCl, dried with anhydrous $MgSO_4$ and the solvent was distilled off. The residue was recrystallized from methanol and dichloromethane to obtain the objective compound 1.36 g (yield: 78%).

Melting point: 251° to 256° C. (decomp.)
Acetate $^1$H-NMR($CF_3COOD$) δ:
2.23(3 H, s, $CH_3CO$)
3.32(3 H, s, $SO_2CH_3$)
3.96(3 H, s, $OCH_3$)
7.12–8.46(14 H, m, aromatic H, NH)

EXAMPLE 23

Synthesis of N-{4-[(7-(2,3,4,6-tetra-O-acetylglycosyl-1-amino)-10H-indolo[3,2-b]quinoline-11-yl)amino]-3-methoxyphenyl} methanesulfonamide

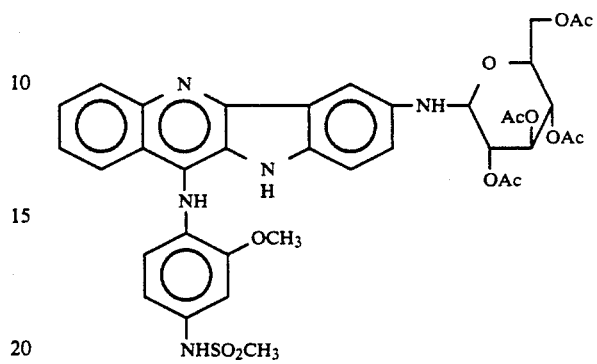

1-Bromo-2,3,4,6-tetra-0-acetylglucose 450 mg (1 mmol) was dissloved in dried pyridine 1 ml and dried dimethyformamide 10 ml and stirred overnight in an atmosphere of argon. Then, to this solution, dimethylformamide solution containing 240 mg (0.5 mmol) of 2-amino-6-(4-methanesulfonamide-2-methoxyanilino)indolo[3,2-b]quinoline obtained in Example 22 was added and reacted for 24 hours at room temperature. The reaction solution was poured into ice water and extracted with chloroform. The solvent was distilled off from the resulting chloroform solution and the residue was subjected to silica gel column chromatography to obtain the objective compound 210 mg (yield: 30%) from the dichloromethane:hexane (1:5) eluate.

Melting point: 172° to 178° C. (decomp.)
$^1$H-NMR(DMSO–$d_6$) δ:
2.08(12 H, s, $COCH_3 \times 4$)
2.96(3 H, s, $SO_2CH_3$)
4.04(3 H, s, $OCH_3$)
4.16–4.64(3 H, m, 4'—H, $CH_2OAc$)
5.11–5.39(2 H, m, 2'—H, 3'—H)
5.71–6.00(1 H, m, 5'—H)
6.48–6.68(1 H, m, 1'—H)
7.14–7.79(10 H, m, aromatic H, NH)
8.09–8.74(3 H, m, aromatic H)

EXAMPLE 24

Synthesis of N-{4-[(7-(glycosyl-1-amino)-10H-indolo[3,2-b]quinoline-11-yl)amino]-3-methoxyphenyl} methanesulfonamide

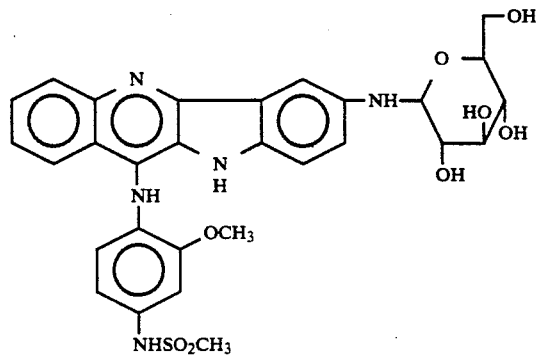

120 mg (0.14 mmol) of N-{4-[(7-(2,3,4,6-tetra-O-acetylglycosyl-1-amino)-10H-indolo[3,2-b]quinoline-11-yl) amino]-3-methoxyphenyl} methanesulfonamide obtained in Example 23 was dissolved in methanol 20 ml and an aqueous ammonium solution (NH₃.H₂O) 20 ml. The resulting solution was agitated for 3 days and during this agitation, ammonia was added to this solution every 3 hours. The reaction solution was neutralized with 10% aqueous acetic acid solution and methanol was distilled off from the neutralized solution. Deposited crystals were collected by filtration and recrystallized from methanol and dichloromethane to obtain the objective compound 75 mg (yield: 87%).

Melting point: 201° to 205° C. (decomp.)
$^1$H-NMR(CD₃OD+DMSO−d₆)
2.96(3 H, s, SO₂CH₃)
3.73(2 H, s, CH₂OH)
4.04(3 H, s, OCH₃)
4.55(6 H, m, 4'—H, 5'—H and OH×4)
5.03–5.12(2 H, m, 2'—H and 3'—H)
6.36–6.52(1 H, m, 1'—H)
6.58–6.64(1 H, m, aromatic H)
7.14–7.79(10 H, m, aromatic H, NH)
7.94–8.56(3 H, m, aromatic H)

EXAMPLE 25

Synthesis of 2-methylcarbamoyl 6-(4-methanesulfonamide-2-methoxyanilino)indolo[3,2-b]quinoline

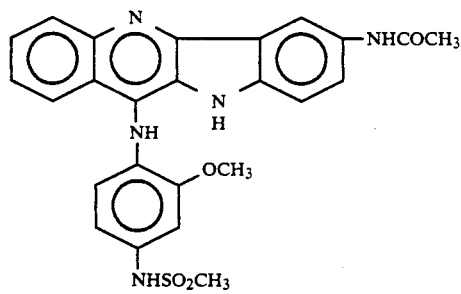

500 mg (1.1 mmol) of 2-amino-6-(4-methanesulfonamide-2-methoxyanilino)indolo[3,2-b]quinoline obtained in Example 22 was dissolved in dried pyridine 10 ml and acetic anhydride 2 ml and heated at 80° to 90° C. for 6 hours. The reaction solution was poured into ice water and extracted with chloroform. The resulting chloroform solution was washed with water and dried with anhydrous MgSO₄. The solvent was distilled off and the residue was recrystallized from tetrahydrofuran and dichloromethane to obtain the objective compound 470 mg (yield: 75%)

Melting point: 223° to 226° C. ( decomp.)
$^1$H-NMR(CF₃COOD) δ:
2.08(3 H, s, COCH₃)
3.28(3 H, s, SO₂OH₃)
3.80(3 H, s, OCH₃)
7.08–7.86(9 H, m, aromatic H, NH)
7.89–8.48(5 H, m, aromatic H, NH)

EXAMPLE 26

Synthesis of hydrochloride of 2-methanesulfonamide-6-(4-methanesulfonamide-2-methoxyanilino)indolo[3,2-b]quinoline

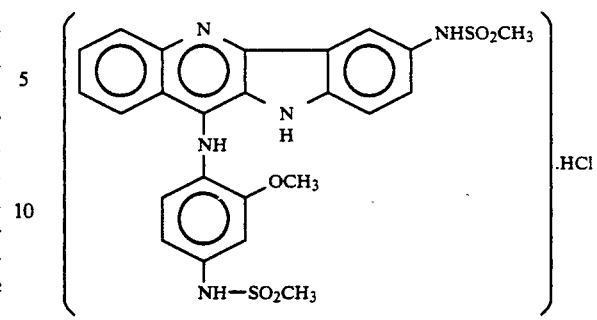

500 mg (1.1 mmol) of 2-amino-6-(4-methanesulfonamide-2-methoxyanilino)indolo[3,2-b]quinoline obtained in Example 22 was dissolved in dried pyridine 10 ml and to this solution, CH₃SO₂Cl 132 mg (1.05 equivalent) was added dropwise at 0° C. After addition, the reaction solution was agitated for 3 hours and poured into ice water. Deposited crystals were collected by filtration and recrystallized from chloroform and methanol to obtain the objective compound 520 mg (yield: 90%).

Melting point: 251° to 255° C. ( decomp.)
$^1$H-NMR(CF₃COOD) δ:
2.90(3 H, s, 7-NHSO₂CH₃)
3.31(2 H, s, 4'-NHSO₂CH₃)
3.82(3 H, s, OCH₃)
7.01–7.25(3 H, m, aromatic H)
7.25–7.99(8 H, m, aromatic H, NH)
8.02–8.41(3 H, m, aromatic H)

EXAMPLE 27

Synthesis of hydrochloride of 6-(4-methanesulfonamide-2-methoxyanilino)-10-methylbenzofurano[3,2-b]quinoline

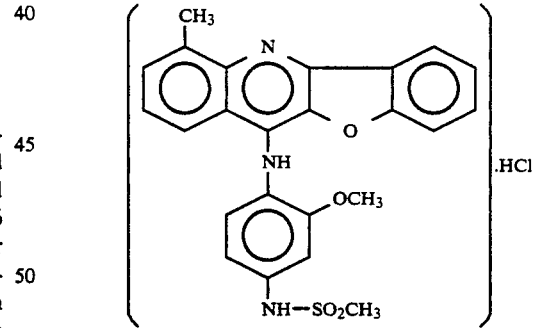

3-Methylanthranilic acid 5 g (33 mmol) was dissolved in 10% aqueous sodium hydroxide solution 27 ml and to this solution, phenoxyacetyl chloride 6.2 g (36 mmol) was added dropwise at 0° C. The resulting solution was stirred at room temperature for 1 hour and acidified with 10% hydrochloric acid solution. Deposited crystals were collected by filtration, washed with water and recrystallized from ethanol to obtain 3-methyl-N-(phenoxyacetyl)anthranilic acid (melting point: 174° to 176° C.) 4.4 g (yield: 47%).

This compound 7.6 g (27 mmol) was mixed with polyphosphoric acid 60 g and heated with stirring at 120° to 130° C. for 1.5 hours. The reaction mixture was poured into ice water and neutralized with potassium hydrogencarbonate. Deposited crystals were collected by filtration to obtain 10-methyl-6,11-dihydrobenzofurano[3,2-b]quinoline-6-one 5.0 g (yield: 74%). Then, this compound 5.0 g was added to phosphorus oxychloride 50 ml and heated under reflux for 1 hour. Unreacted phosphorus oxychloride was distilled off under the reduced pressure, and the residue was neutralized with an aqueous KOH solution and extracted with chloroform. The resulting chloroform solution was washed with water and dried, and then the solvent was distilled off. The residue was recrystallized from benzene to obtain 6-chloro-10-methylbenzofurano[3,2-b]quinoline (melting point: 137° to 139° C.) 4.1 g (yield: 54%).

This compound 1.8 g (5.0 mmol) and 4-amino-3-methoxyanilinomethanesulfonamide 1.6 g (7.4 mmol) were dissolved in 15 ml of ethoxyethanol and heated under reflux for 15 hours. Deposited crystals were collected by filtration and washed with ether to obtain the objective compound (hydrochloride) 0.8 g (yield: 36%).

Melting point: 255° to 259° C.
I R $\nu_{max}^{Nujol}$ cm$^{-1}$:1640(S=O), 3300(NH)
$^1$H-NMR (CDCl$_3$+DMSO−d$_6$) δ:
2.96(6 H, s, 4—CH$_3$, SO$_2$CH$_3$)
3.93(3 H, s, OCH$_3$)
6.70–6.95, 7.18–7.75, 8.55–8.95(12 H, m, aromatic H, NH×2)

EXAMPLE 28

Synthesis of hydrochloride of 6-(4-methanesulfonamide-2-methoxyanilino)-1,10-dimethylbenzofurano[3,2-b]quinoline

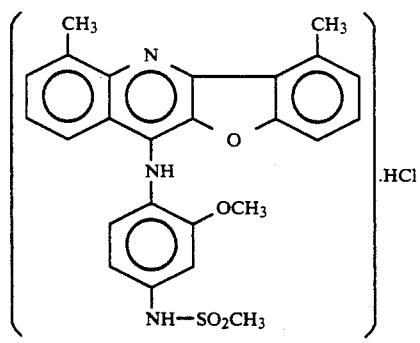

3-Methylanthranilic acid 1.0 g (6 mmol) was dissolved in 10% aqueous sodium hydroxide solution 27 ml and to this soulution, 2-methylphenoxyacetyl chloride 1.3 g (7.3 mmol) was added dropwise at 0° C. The resulting solution was stirred at room temperature for 5 minutes and acidified with 10% hydrochloric acid solution. Deposited crystals were collected by filtration, washed with hot water and recrystallized from ethanol to obtain 3-methyl-N-(2-methylphenoxyacetyl)anthranilic acid (melting point: 133° to 136° C.) 1.7 g (yield: 83%).

This compound 19.4 g (65 mmol) was mixed with polyphosphoric acid 650 g and heated with stirring at 120° C. for 2 hours. The reaction mixture was poured into ice water and deposited crystals were collected by filtration to obtain a mixture (6.4 g) of 1,10-dimethyl-6,11-dihydrobenzofurano[3,2-b]quinoline-6-one and 3,10-dimethyl-6,11-dihydrobenzofurano[3,2-b]quinoline-6-one. Then, this mixture 6.4 g was added to phosphorus oxychloride 25 ml and heated under reflux for 0.5 hours. Unreacted phosphorus oxychloride was distilled off under the reduced pressure, and the residue was poured into ice water and extracted with ethyl acetate. The resulting ethyl acetate solution was dried with anhydrous MgSO$_4$, and then the solvent was distilled off. The residue was subjected to silica gel column chromatography to obtain 6-chloro-1,10-dimethylbenzofurano[3,2-b]quinoline (melting point: 165° to 168° C.) 0.9 g (yield: 14%) and 6-chloro-3,10-dimethylbenzofurano[3,2-b]quinoline (melting point: 164° to 168° C.) 2.2 g (yield: 33 %).

Then, the 1,10-dimethyl compound 0.5 g (1.6 mmol) and 4-amino-3-methoxyanilinemethanesulfonamide hydrochlorate 0.5 g (2.0 mmol) were dissolved in 5 ml of ethoxyethanol and heated under reflux for 2 hours. The reaction solution was neutralized with an aqueous solution saturated with KHCO$_3$ and extracted with ethyl acetate. The resulting ethyl acetate solution was dried with anhydrous MgSO$_4$ and the solvent was distilled off. The residue was subjected to silica gel column chromatography to obtain the objective compound (hydrochloride) 0.3 g (yield: 38%).

Melting point: 211° to 213° C.
I R $\nu_{max}^{Nujol}$ cm$^{-1}$:3510, 3300, 1320
$^1$H-NMR (CF$_3$COOD) δ:
2.93(3 H, s, CH$_3$)
3.15(3 H, s, CH$_3$)
3.33(3 H, s, SO$_2$CH$_3$)
3.87(3 H, s, OCH$_3$)
6.95–8.10(8 H, m, aromatic H)
8.15–8.45(1 H, dd, J=8.2 Hz, aromatic H)

EXAMPLE 29

Synthesis of hydrochloride of 6-(4-methanesulfonamide-2-methoxyanilino)-3,10-dimethylbenzofurano[3,2-b]quinoline

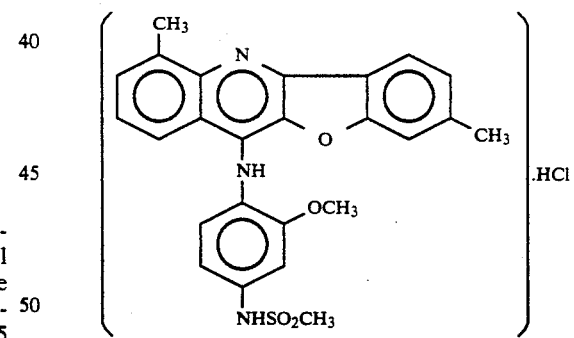

0.35 g (1.2 mmol) of 6-chloro-3,10-dimethyl-benzofurano[benzofurano[3,2-b]quinoline obtained in Example 28 and 4-amino-3-methoxyanilinemethanesulfonamide hydrochlorate 0.4 g (1.8 mmol) were dissolved in 5 ml of ethoxyethanol and heated under reflux for 6 hours. After cooling, deposited crystals were collected by filtration and washed with ethanol to obtain the objective compound 0.4 g (yield: 61%).

Meltign point: 179° to 184° C.
$^1$H-NMR (CF$_3$COOD) δ:
2.59(3 H, s, CH$_3$)
2.87(3 H, s, CH$_3$)
3.28(3 H, s, SO$_2$CH$_3$)
3.84(3 H, s, OCH$_3$)
7.00–8.27(9 H, m, aromatic H)

EXAMPLE 30

Synthesis of hydrochloride of 6-(4-methanesulfonamide-2-methoxyanilino)-1-methylbenzofurano[3,2-b]quinoline

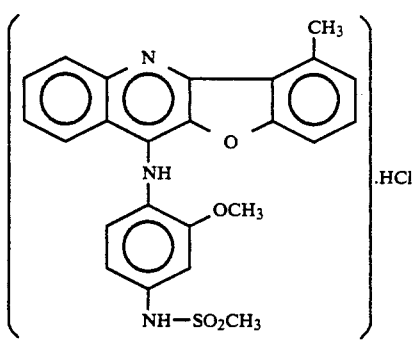

Anthranilic acid 7.95 g (58 mmol) was dissolved in 10% aqueous sodium hydroxide solution 48 ml and to this solution, 3-methylphenoxyacetyl chloride 11.8 g (64 mmol) was added dropwise at 0° C. The resulting solution was stirred at room temperature for 5 minutes and acidified with 10% hydrochloric acid solution. Deposited crystals were collected by filtration and washed with hot water to obtain N-(3-methylphenoxyacetyl)anthranilic acid 14.0 g (yield: 68%).

This compound 14.0 g (44 mmol) was mixed with polyphosphoric acid 467 g and heated with stirring at 120° C. for 2 hours. The reaction mixture was poured into ice water, and deposited crystals were collected by filtration and washed with 10 % KHCO$_3$ solution and water to obtain a mixture (6.5 g) of 1-methyl-6,11-dihydrobenzofurano[3,2 -b]quinoline-6-one and 3-methyl-6,11-dihydrobenzofurano[3,2-b]quinoline-6-one. Then, this mixture 6.5 g was added to phosphorus oxychloride 20 ml and heated under reflux for 1 hour. Unreacted phosphorus oxychloride was distilled off under the reduced pressure, and the residue was poured into ice water and neutralized with an aqueous solution saturated with KHCO$_3$. Deposited crystals were collected by filtration and washed with water. Thus obtained crystals were subjected to silica gel column chromatography to obtain 6-chloro-1-methylbenzofurano[3,2-b]quinoline (melting point: 169° to 172° C.) 0.48 g (yield: 4%) from the hexane eluate and 6-chloro-3-methylbenzofurano[3,2-b]quinoline 3.42 g (yield: 26%) from the next eluate (hexane:ethyl acetate = 8:1).

Then, the 1-methyl compound 0.45 g (1.6 mmol) and 4-amino-3-methoxyanilinemethanesulfonamide 0.44 g (1.7 mmol) were dissolved in 5 ml of ethoxyethanol and heated under reflux for 3.3 hours. Deposited crystals were collected by filtration and washed with ethanol to obtain the objective compound (hydrochloride) 0.6 g (yield: 76%).

Melting point: 253° to 255° C.

I R $\nu_{max}^{Nujol}$ cm$^{-1}$: 3510, 3300, 1320

$^1$H-NMR (DMSO—d$_6$)
3.00(6 H, s, CH$_3$, SO$_2$CH$_3$)
3.69(3 H, s, OCH$_3$)
6.98-8.47(12 H, m, aromatic H, NH)

EXAMPLE 31

Synthesis of hydrochloride of 6-(4-methanesulfonamide-2-methoxyanilino)-3-methylbenzofurano[3,2-b]quinoline

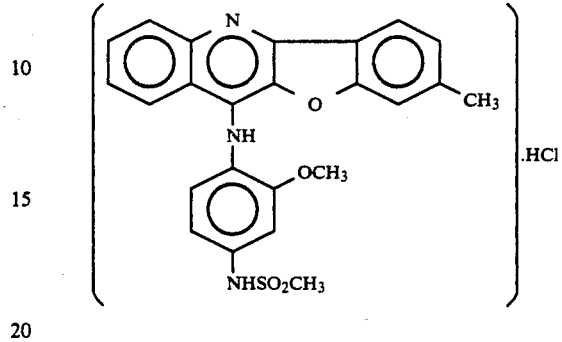

6-Chloro-3-methylbenzofurano[3,2-b]quinoline (0.4 g (1.6 mmol)) obtained in Example 30 and 4-amino-3-methoxyanilinemethanesulfoniamide hydrochlorate 0.44 g (1.7 mmol) were dissolved in 5 ml of ethoxyethanol and heated under reflux for 2 hours. Deposited crystals were collected by filtration and washed with ethanol to obtain the objective compound 0.64 g (yield: 81%).

Melting point: 213° to 215° C.
$^1$H-NMR (DMSO—d$_6$) δ:
2.45(3 H, s, CH$_3$)
3.00(3 H, s, SO$_2$CH$_3$)
3.65(3 H, s, OCH$_3$)
6.85-8.20(10 H, m, aromatic H)

EXAMPLE 32

Synthesis of hydrochloride of 6-(4-methanesulfonamide-2-methoxyanilino)-10-methylbenzothieno[3,2-b]quinoline

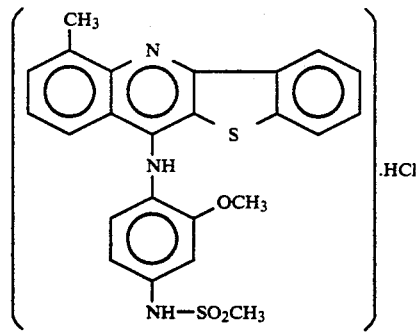

Benzenethiol and butyl bromoacetate were reacted by a conventional method and then hydrolyzed to obtain α-phenylthioacetatic acid. α-phenylthioacetatic acid was reacted with thionyl chloride by a convention method to obtain α-phenylthioacetyl chloride. 3-Methylanthranilic acid 5g (33 mmol) was dissolved in 10% aqueous sodium hydroxide solution 27 ml and to this solution, α-phenylthioacetyl chloride 5.5 ml (33 mmol) was added dropwise at 0° C. The resulting solution was stirred at room temperature for 1 hour and neutralized with 10% hydrochloric acid solution. Deposited crystals were collected by filtration and recrystallized from ethanol and water to obtain 3-methyl-N-

(phenylthioacetyl)anthranilic acid (melting point: 148° to 150° C.) 8.8 g (yield: 89%).

This compound 4.6 g (15 mmol) was mixed with polyphosphoric acid 30 g and heated with stirring at 120° to 130° C. for 2 hours. The reaction mixture was poured into ice water and neutralized with potassium hydrogencarbonate. Deposited crystals were collected by filtration and washed with water to obtain 10-methylbenzothieno[3,2-b]-6,11-dihydroquinoline-6-one 4.2 g (yield: 90%).

Then, this compound 4.2 g was added to phosphorus oxychloride 50 ml and heated under reflux for 2.5 hours. Unreacted phosphorus oxychloride was distilled off under the reduced pressure, and the residue was poured into ice water, neutralized with an aqueous KHO solution and extracted with chloroform. The resulting chloroform solution was washed with water and dried, and then the solvent was distilled off. The residue was recrystallized from benzene to obtain 6-chloro-10-methylbenzothieno[3,2-b]quinoline (melting point: 143° to 146° C.) 4.1 g (yield: 84%).

Then, this compound 1 g (3.7 mmol) and 4-amino-3-methoxyanilinemethanesulfonamide 1.2 g (4.4 mmol) were dissolved in 12 ml of ethoxyethanol and heated under reflux for 1.5 hours. Deposited crystals were collected by filtration, stirred in chloroform with $KHCO_3$ and extracted with chloroform. The resulting chloroform solution was dried with anhydrous $MgSO_2$ and the solvent was distilled off. The residue was recrystallized from acetone to obtain the objective compound (hydrochloride) 0.8 g (yield: 48%).

Melting point: 220° to 223° C.
I R $\nu_{max}^{Nujol}$ cm$^{-1}$: 3400, 3250, 1320
$^1$H-NMR (DMSO—$d_6$) δ:
3.11(3 H, s, 4-$CH_3$)
3.28(3 H, s, $SO_2CH_3$)
3.66(3 H, s, $OCH_3$)
6.63–8.70(12 H, m, aromatic H, NH×2)

EXAMPLE 33

Synthesis of hydrochloride of 6-(4-methanesulfonamide-2-methoxyanilino)-1-methylbenzothieno[3,2-b]quinoline

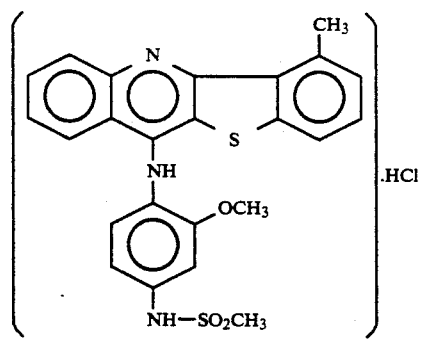

3-Methylbenzenethiol and butyl bromoacetate were reacted by a conventional method and then hydrolyzed to obtain 3-methyl-α-phenylthioacetatic acid. 3-Methyl-α-phenylthioacetatic acid was reacted with thionyl chloride by a conventional method to obtain 3-methyl-α-phenylthioacetyl chloride. Anthranilic acid 5.6 g (4.1 mmol) was dissolved in 10% aqueous sodium hydroxide solution 32 ml and to this solution, 3-methyl-α-phenylthioacetyl chloride (99° C./3.3 mmHg) 8.9 g was added dropwise at 0° C. The resulting solution was stirred at room temperature for 20 minutes and neutralized with 10% hydrochloric acid solution. To this solution, ether was added, and deposited crystals were collected by filtration and washed with hot water to obtain N-(3-methylphenylthioacetyl)anthranilic acid (melting point: 148° to 150° C.) 11.2 g (yield: 25%).

This compound 15.8 g (50 mmol) was mixed with polyphosphoric acid 500 g and heated with stirring at 120° C. for 2 hours. The reaction mixture was poured into ice water and neutralized with an aqueous potassium hydrogencarbonate solution. Deposited crystals were collected by filtration and washed with water to obtain crude 1-methylbenzothieno[3,2-b]-6,11-dihydroquinoline-6-one 10.5 g.

Then, this compound 10.5 g was added to phosphorus oxychloride 50 ml and heated under reflux for 1 hour. Unreacted phosphorus oxychloride was distilled off under the reduced pressure, and the residue was poured into ice water, neutralized with an aqueous solution saturated with $KHCO_3$ and extracted with chloroform. The resulting chloroform solution was dried with anhydrous $MgSO_4$, and then the solvent was distilled off. The residue was subjected to silica gel column chromatography to obtain 6-chloro-1-methylbenzothieno[3,2-b]quinoline (melting point: 143° to 146° C.) 0.8 g (yield: 6%).

Then, this compound 0.2 g (0.7 mmol) and 4-amino-3-methoxyanilinemethanesulfonamide 0.2 g (0.8 mmol) were dissolved in 5 ml of ethoxyethanol and heated under reflux for 3 hours. Deposited crystals were collected by filtration and washed with ethanol to obtain the objective compound (hydrochloride) 0.21 9 (yield: 60%).

Melting point: 205° to 210° C.
$^1$H-NMR ($CF_3COOD$) δ:
3.04(3 H, s, $CH_3$)
3 33(3 H, s, $SO_2CH_3$)
3.93(3 H, s, $OCH_3$)
7.32–9.02(12 H, m, aromatic H, NH)

Test Example 1: Test for Antitumorigen Function
Function for Inhibiting Multiplication of KB Cell (in vitro test)

KB cells, carcinomatous cell tumors, were transferred to in vitro floatation incubator systems, and added respectively with compounds of Examples 1 to 33. The results of cultivation added with these compounds were compared with the results of the control which was not added with any compound.

① Experimental System:
Cell used: KB Cell (Originating from human mouth epidermal cancer)
Culture medium: Eagles minimal essential medium (MEM) supplemented with 10% calf serum
Cultivation: 37° C. carbon dioxide gas incubator (5% $CO_2$)

② Method of Experiment:
Day 0: KB cells were diluted in the culture medium to adjust the KB cell density to $2\times10^4$/ml. Three ml of the cell suspension was inoculated in each of 60 mm plastic dishes. Two dishes per standard dosage were used.
Day 1: Test compound was added to the medium so that the final concentrations were set to 100, 30, 10, 3 and 1 μg/ml.
Day 4: Cells were scraped off from the dish using trypsin, and the cell number was countered using a Corter counter.

③ Criteria for Judgement:

In generally accordance with the stipulations set forth by the National Cancer Institute (NCI) U.S.A., the concentration of compound necessary for exerting 50% growth inhibition ($ED_{50}$) compared to the contral was determined. A compound was judged as effective when $ED_{50}$ was less than 4 μg/ml.

The results are shown below.

TABLE 1

Results of Test on Carcinostatic Effect
(Effect of Inhibiting growth of KB-Cell)

| Compound No. Tested | Conc.($ED_{50}$)(μg/ml) |
|---|---|
| 1 | <0.3 |
| 2 | <0.3 |
| 3 | <0.3 |
| 4 | <0.3 |
| 5 | <0.3 |
| 6 | <0.3 |
| 7 | <0.3 |
| 8 | <0.3 |
| 9 | <0.3 |
| 10 | <0.3 |
| 11 | <0.3 |
| 12 | <0.3 |
| 13 | <0.3 |
| 14 | <0.3 |
| 15 | <0.3 |
| 16 | <0.3 |
| 17 | <0.3 |
| 18 | <0.3 |
| 19 | <0.3 |
| 20 | <0.3 |
| 21 | <0.3 |
| 22 | <0.3 |
| 23 | <0.3 |
| 24 | <0.3 |
| 25 | <0.3 |
| 26 | <0.3 |
| 27 | 0.38 |
| 28 | <0.3 |
| 29 | <0.3 |
| 30 | 1.5 |
| 31 | <0.3 |
| 32 | 1.4 |
| 33 | <0.3 |
| Reference | 0 |

Test Example 2: Effect on Prolongation of Life Span in Cancer Inplanted Mouse and Acute Toxicity Pharmacological effects of compounds of Examples 1 to 33 were tested in in vitro systems using P-388 implanted mice. The results were compared to that of a control which was to added with any compound.

① System used in experiment:
Animal used: CDF mouse (6 mice/group)
Tumor: P-388
Number of implanted cells: $10^6$ cells/mouse
Implanted site: i.p.
Day of administration: Day 1 and Day 5
Dosage: $LD_{50}$ or 400 mg/kg/day at the maximum
② Criteria for Judgement:

The treatment was judged as effective when the ratio of survival of the treated group to that of the control group (T/C %) was 120% or more. The survival period of the control group was generally about 10 days. The results are shown in Table 2.

TABLE 2

Effect on Prolongation of Life Span of Mouse implanted with P-38 Cancer Cells

| Compound No. Tested | Dosage (mg/kg) | Ratio of Life Prolongation (%) |
|---|---|---|
| 1 | 200 | 240(cure 1/6) |

TABLE 2-continued

Effect on Prolongation of Life Span of Mouse implanted with P-38 Cancer Cells

| Compound No. Tested | Dosage (mg/kg) | Ratio of Life Prolongation (%) |
|---|---|---|
| | 100 | 290(cure 1/6) |
| | 50 | 210 |
| 2 | 400 | 97 |
| | 200 | 99 |
| | 100 | 257(cure 1/6) |
| 3 | 400 | 0 |
| | 200 | 97 |
| | 100 | 151 |
| 4 | 50 | 210 |
| | 25 | 168 |
| | 12.5 | 134 |
| 5 | 400 | 165 |
| | 200 | 172 |
| | 100 | 163 |
| | 50 | 135 |
| | 25 | 140 |
| 6 | 400 | 148 |
| | 200 | 247(cure 2/6) |
| | 100 | 169 |
| 7 | 200 | 111 |
| | 100 | 108 |
| | 50 | 111 |
| 8 | 400 | 155 |
| | 200 | 178 |
| | 100 | 175 |
| 9 | 50 | 305(cure 4/6) |
| | 25 | 235(cure 1/6) |
| | 12.5 | 198 |
| | 6.25 | 168 |
| | 3.12 | 165 |
| | 1.56 | 131 |
| 10 | 100 | 260(cure 1/6) |
| | 50 | 223 |
| | 25 | 203 |
| | 12.5 | 165 |
| | 6.25 | 145 |
| | 3.12 | 109 |
| 11 | 50 | 315(cure 1/6) |
| | 25 | 294(cure 2/6) |
| | 12.5 | 315(cure 1/6) |
| 12 | 50 | 315(cure 1/6) |
| | 25 | 242(cure 1/6) |
| | 12.5 | 231 |
| 13 | 50 | 115 |
| | 25 | 192 |
| | 12.5 | 189 |
| 14 | 200 | 221 |
| | 100 | 266(cure 1/6) |
| | 50 | 282 |
| 15 | 200 | 76 |
| | 100 | 240(cure 1/6) |
| | 50 | 263 |
| 16 | 50 | 269 |
| | 25 | 288(cure 2/6) |
| | 12.5 | 240(cure 2/6) |
| 17 | 50 | 75 |
| | 25 | 77 |
| | 12.5 | 153 |
| 18 | 50 | 70 |
| | 25 | 131 |
| | 12.5 | 164(cure 1/6) |
| 19 | 50 | 93 |
| | 25 | 252(cure 2/6) |
| | 12.5 | 313(cure 3/6) |
| 20 | 50 | 202 |
| | 25 | 131(cure 1/6) |
| | 12.5 | 179 |
| 21 | 100 | 212 |
| | 50 | 185(cure 1/6) |
| | 25 | 179 |
| 22 | 50 | 242(cure 1/6) |
| | 25 | 200 |
| | 12.5 | 171 |
| 23 | 50 | 58 |
| | 25 | 148(cure 1/6) |
| | 12.5 | 300(cure 2/6) |
| 24 | 50 | 90 |

TABLE 2-continued

Effect on Prolongation of Life Span of Mouse implanted with P-38 Cancer Cells

| Compound No. Tested | Dosage (mg/kg) | Ratio of Life Prolongation (%) |
|---|---|---|
|  | 25 | 145 |
|  | 12.5 | 213(cure 2/6) |
| 25 | 50 | 184 |
|  | 25 | 174 |
|  | 12.5 | 135 |
| 26 | 50 | 143 |
|  | 25 | 111 |
|  | 12.5 | 126 |
| 27 | 400 | 310(cure 2/6) |
|  | 200 | 250(cure 1/6) |
|  | 100 | 230 |
| 28 | 200 | 103 |
|  | 100 | 269 |
|  | 50 | 204 |
| 29 | 400 | 76 |
|  | 200 | 269(cure 1/6) |
|  | 100 | 204(cure 1/6) |
| 30 | 400 | 151 |
|  | 200 | 108 |
|  | 100 | 105 |
| 31 | 400 | 219(cure 1/6) |
|  | 200 | 175(cure 1/6) |
|  | 100 | 147 |
| 32 | 400 | 228 |
|  | 200 | 167 |
|  | 100 | 137 |
| 33 | 400 | 280(cure 1/6) |
|  | 200 | 255(cure 1/6) |
|  | 100 | 191 |

What we claim is:

1. A condensed quinoline system compound represented by formula (I) or a pharmaceutically acceptable salt thereof:

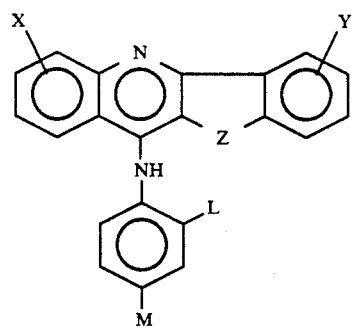

wherein Z is —NH, L is a lower alkoxy, m is NHQ, wherein Q is —SO$_2$CH$_3$, X is hydrogen, Y is —NHR, wherein R is:

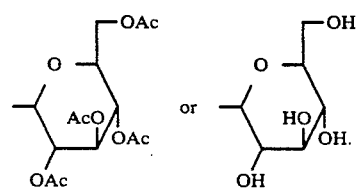

2. A condensed quinoline system compound of claim 1, wherein R is:

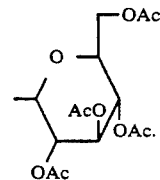

3. A condensed quinoline system compound of claim 1 wherein R is:

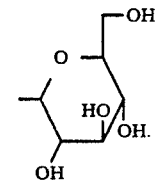

4. The condensed quinoline compound of claim 1, wherein said pharmaceutically acceptable salt is selected from the group consisting of a hydrochloric acid salt, a phosphoric acid salt, a bromic acid salt, a sulfuric acid salt, a benzoic acid salt, a citric acid salt, a succinic acid salt, an acetic acid salt, a tartaric acid salt and a maleic acid salt.

* * * * *